US011331217B2

(12) United States Patent
Schaller

(10) Patent No.: US 11,331,217 B2
(45) Date of Patent: May 17, 2022

(54) DEVICES AND METHODS FOR CREATING A CAPSULORHEXIS

(71) Applicant: Michael Schaller, Louisville, CO (US)

(72) Inventor: Michael Schaller, Louisville, CO (US)

( * ) Notice: Subject to any disclaimer, the term of this patent is extended or adjusted under 35 U.S.C. 154(b) by 147 days.

(21) Appl. No.: 16/616,667

(22) PCT Filed: May 25, 2018

(86) PCT No.: PCT/US2018/034767
§ 371 (c)(1),
(2) Date: Nov. 25, 2019

(87) PCT Pub. No.: WO2018/218221
PCT Pub. Date: Nov. 29, 2018

(65) Prior Publication Data
US 2020/0085619 A1    Mar. 19, 2020

Related U.S. Application Data

(60) Provisional application No. 62/511,083, filed on May 25, 2017.

(51) Int. Cl.
*A61F 9/007* (2006.01)
*A61B 34/30* (2016.01)
*A61B 17/00* (2006.01)
*A61F 9/008* (2006.01)

(52) U.S. Cl.
CPC .......... *A61F 9/00754* (2013.01); *A61B 34/30* (2016.02); *A61B 2017/00862* (2013.01); *A61B 2017/00867* (2013.01); *A61B 2217/005* (2013.01); *A61B 2217/007* (2013.01); *A61F 2009/00844* (2013.01); *A61F 2009/00872* (2013.01); *A61F 2009/00889* (2013.01)

(58) Field of Classification Search
CPC ........ A61F 9/00754; A61F 2009/00844; A61F 2009/00872; A61F 2009/00889; A61B 34/30; A61B 2017/00862; A61B 2017/00867; A61B 2217/005; A61B 2217/007
See application file for complete search history.

(56) References Cited

U.S. PATENT DOCUMENTS 8,137,344 B2 *  3/2012  Jia ..................... A61F 9/00754
606/45

* cited by examiner

*Primary Examiner* — Tan-Uyen T Ho
*Assistant Examiner* — Chima U Igboko
(74) *Attorney, Agent, or Firm* — Aurora Consulting LLC; Ashley Sloat

(57) ABSTRACT

Described herein are devices and methods for creating a capsulorhexis. In some embodiments, the device includes a template with a tearing profile, which, when placed against the capsular bag, defines a perimeter of a capsulorhexis. In some embodiments, the device further includes rigid sections and bendable sections which are configured to transition the template between a first bent configuration for insertion through a corneal incision and a second unbent configuration for creation of the capsulorhexis. In some embodiments, the device further includes connecting elements which enter through the corneal incision and, when manipulated, transition the device between the first bent configuration and the second unbent configuration. In some embodiments, the connectors are configured to impart a downward force on the template and thus the capsular bag during the capsulorhexis creation.

15 Claims, 21 Drawing Sheets

DEVICES AND METHODS FOR CREATING A CAPSULORHEXIS

CROSS-REFERENCE TO RELATED APPLICATIONS

This application is the U.S. National Phase Application for International PCT Application Ser. No. PCT/US2018/034767, filed May 25, 2017; which claims the priority benefit of U.S. Provisional Patent Application Ser. No. 62/511,083, filed May 25, 2017, entitled "Capsulorhexis Tool and Method," both of which are herein incorporated by reference in their entireties.

INCORPORATION BY REFERENCE

All publications and patent applications mentioned in this specification are herein incorporated by reference in their entirety, as if each individual publication or patent application was specifically and individually indicated to be incorporated by reference in its entirety.

TECHNICAL FIELD

This disclosure relates generally to the field of ocular surgery, and more specifically to the field of cataract surgery. Described herein are devices and methods for creating a capsulorhexis in an eye.

BACKGROUND

During cataract surgery, the surgeon creates an opening in the capsular bag of a patient's eye, typically called a capsulorhexis or capsulotomy. Traditionally, a pair of forceps is used to tear the capsulorhexis in the capsular bag. Clinically, it is important that the opening be close to a perfect circle and centered about the optical axis of the eye. Additionally, it is important that the tear is continuous and does not present any small breaks that allow a separate tear to propagate posteriorly. Therefore, the capsulorhexis is an important part of the cataract procedure and can present a challenge for the surgeon. The surgeon must carefully pull with a force vector such that the tear propagates along a circular path.

Several devices have been developed to assist in the creation of the capsulorhexis or capsulotomy. For example, femtosecond lasers have been developed to create the opening. However, these are expensive pieces of capital equipment, and additionally, the laser cut profile of the capsulotomy created with these lasers is not the same as the torn profile created during the manual capsulorhexis. Additionally, other devices using energy (e.g., RF energy) have been discussed that place a cutting filament onto the capsular bag intraocularly. However, again the cut profile of these devices is not the same as the torn profile created during manual capsulorhexis, and they also require expensive capital equipment and new training of the surgeon. Other devices have been discussed that use a variety of sharp cutting blades that rotate on the surface of the capsular bag or push down on the surface to create the capsulorhexis. Again, the cut profile may be different than the manual capsulorhexis tearing method, and these devices are sometimes complicated or difficult to insert through a standard corneal incision especially if they include sharp blade profiles.

SUMMARY

Described herein are devices and methods for creating a consistent capsulorhexis that produces a similar torn profile to the traditional manual capsulorhexis. The device includes a template that is approximately the size of a desired capsulorhexis, in the range of 3.0 mm to 7.0 mm, that may be placed intraocularly on top of the capsular bag of the patient. The devices described herein allow the surgeon to tear the capsular bag within or substantially within the center of the template. The template directs the tearing along the circumferential profile of the template such that a circular capsulorhexis is created. The device and method may also prevent the tear from propagating posteriorly. Additionally, the device and method may include features which center the template about the optical axis of the patient.

Additionally, the template may have one or more foldable areas or flexible areas configured to be folded. Such areas allow the template to be bent or folded such that it may be inserted into the eye through a relatively small incision and then unbent or unfolded onto the capsular bag. The foldable area may be a flexible piece of material that may be bent. The template may also include a template backer which provides relative rigidity to the non-foldable areas. The template backers may be used to provide a downward force on the capsular bag during the capsulorhexis procedure.

One aspect of the present disclosure is directed to a device for creating a capsulorhexis. In some embodiments, the device includes a first side comprising a tearing profile configured to be positioned against a capsular bag of a patient; a second side opposite the first side; and one or more bendable sections defining a first portion and a second portion.

In some embodiments, the device is transitionable between a first configuration and a second configuration.

In some embodiments, in the first configuration, the device is configured to bend about the one or more bendable sections for insertion through a corneal incision into an anterior chamber of an eye.

In some embodiments, in the second configuration, the device is configured to unbend about the one or more bendable sections after insertion through the corneal incision into the anterior chamber of the eye.

In some embodiments, in the first configuration, at least a part of the second side of the first portion is folded adjacent to at least a part of the second side of the second portion.

In some embodiments, the device further comprises one or more rigid sections in one or more of the first portion and the second portion.

In some embodiments, the one or more rigid sections are configured to not bend substantially during insertion into the anterior chamber.

In some embodiments, the one or more rigid sections are each defined by one or more template backers which stiffen the first and second portions.

In some embodiments, the one or more bendable sections are defined by an absence of the one or more template backers.

In some embodiments, the template backers include a layer of rigid material on the second side of the template.

In some embodiments, the one or more template backers each include connector elements which enter through the corneal incision during the capsulorhexis creation.

In some embodiments, the connector elements each include a flexing area that bends during the capsulorhexis creation.

In some embodiments, the bending of the connector elements imparts a downward force on the capsular bag.

In some embodiments, the one or more template backers are configured to press the first side onto the capsular bag with sufficient force to create a tear in the capsular bag.

In some embodiments, in the second configuration, the tearing profile forms a perimeter for a capsulorhexis.

In some embodiments, the tearing profile is substantially circular.

In some embodiments, the diameter of the tearing profile is between 3 mm and 7 mm.

In some embodiments, the device includes two bendable sections and two rigid sections.

In some embodiments, the two bendable sections are configured to bend about a single bending axis.

In some embodiments, in the first configuration, a maximum cross-sectional area of the device as it crosses the corneal incision is less than 3.0 mm$^2$.

Another aspect of the present disclosure is directed to a device for creating a capsulorhexis. In some embodiments, the device includes a template including one or more bendable sections and a tearing profile on a first side; and one or more rigid sections separated by the one or more bendable sections. In some embodiments, the one or more rigid sections are configured to provide a downward force onto the template and capsular bag.

In some embodiments, the one or more rigid sections are coupled to one or more connector elements which enter through a corneal incision during the capsulorhexis creation.

In some embodiments, a rotation of the one or more connector elements transitions the template between a first configuration and a second configuration.

In some embodiments, in the first configuration, the template is in a bent configuration for insertion through a corneal incision having a width of less than 3.0 mm.

In some embodiments, in the second configuration, the template is in an unbent configuration for the creation of the capsulorhexis.

In some embodiments, the one or more connector elements are configured to impart the downward force onto the template.

In some embodiments, the one or more connector elements are configured to flex in a flexing area which imparts the downward force onto the template.

Another aspect of the present disclosure is directed to a system for creating a capsulorhexis. In some embodiments, the system includes a template including a tearing profile on a first side; and one or more connecting elements coupled to the template. In some embodiments, the one or more connecting elements are configured to enter through a corneal incision. In some embodiments, a rotation of the one or more connecting elements relative to one another changes the template between a first bent configuration and a second unbent configuration.

In some embodiments, the template is configured to be inserted through the corneal incision in the first bent configuration.

In some embodiments, the template is configured to press on a capsular bag in the second unbent configuration.

In some embodiments, in the first bent configuration, the cross-sectional area of the template as it is inserted through the corneal incision is less than 3.0 mm$^2$.

In some embodiments, the template further includes one or more rigid sections which stiffen the template.

In some embodiments, the one or more connecting elements are coupled to the rigid sections.

In some embodiments, the template further includes one or more bendable sections defined by an absence of the one or more rigid sections.

In some embodiments, the system further includes a feedback mechanism provided to a user that indicates a location of the tearing profile relative to an optic axis of the eye.

In some embodiments, the feedback mechanism is a visual indicator within an ophthalmic microscope display.

In some embodiments, the feedback mechanism is an audible indicator.

In some embodiments, the system further includes a control interface external to the eye.

In some embodiments, manipulation of the control interface transitions the template between the first bent configuration and second unbent configuration.

In some embodiments, the control interface is a handle assembly.

BRIEF DESCRIPTION OF THE DRAWINGS

The foregoing is a summary, and thus, necessarily limited in detail. The above-mentioned aspects, as well as other aspects, features, and advantages of the present technology are described below in connection with various embodiments, with reference made to the accompanying drawings.

Figure 1:
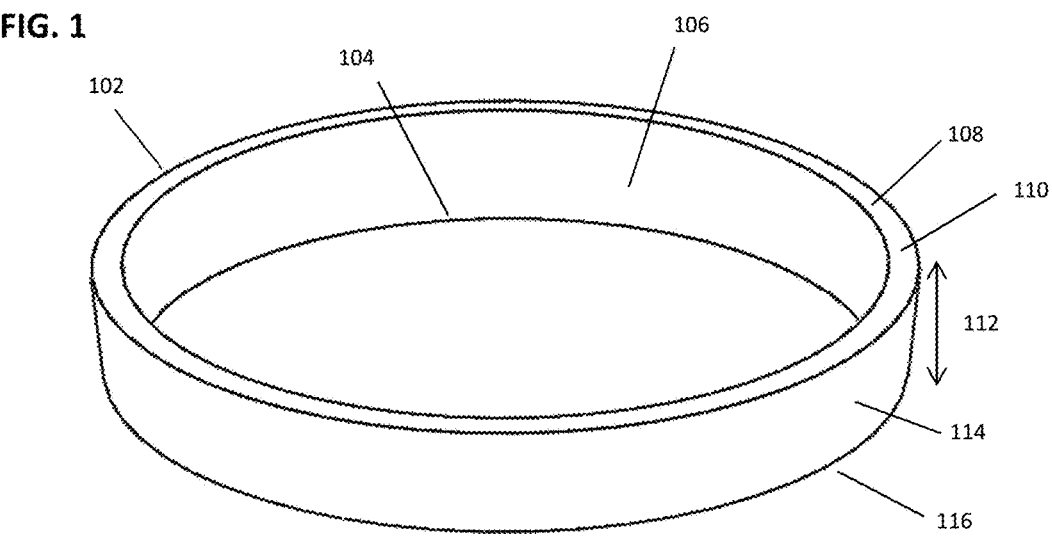
FIG. 1 illustrates an embodiment of a device for creating a capsulorhexis.

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

Template and stencil devices have been described. However, there are several limitations and challenges with these devices which are overcome by certain embodiments described herein. First, in order for a template to be effective it must be in intimate contact with the capsular bag surface and impart a downward force on the capsular bag such that the capsulorhexis tear follows the tearing profile. The capsulorhexis tear should not move beyond the boundary defined by the tearing profile because it may extend posteriorly and cause the capsular bag to split. This is a significant concern for surgeons. Additionally, it is important that the template remains in one place and does not move while the capsulorhexis is being created so that the capsulorhexis is identical to the tearing profile of the template. In some previous devices, a means of manipulating the template and pressing the template down firmly on the capsular bag is not provided or effective.

A second limitation of some previous devices is that the template may not be able to be inserted through a typical corneal incision used in modern cataract surgery. While corneal incisions may vary in size from surgeon to surgeon, generally an incision of less than 3.0 mm is considered advantageous. If a capsulorhexis of approximately 5.0 mm in diameter is preferred, a fully rigid template with a 5.0 mm tearing profile simply cannot be inserted through a 3.0 mm wide incision. Therefore, the device must be deformed in some manner to pass through the incision. Some previous devices attempt to overcome this limitation by stretching the template like a rubber band into an elongate shape that has a narrower width when stretched. However, these devices are generally flexible and not sufficiently rigid because they are required to transition from a circular shape to a stretched rubber band shape during insertion into the eye. Therefore, these previous devices are not rigid enough to be depressed firmly onto the surface of the capsular bag to create the capsulorhexis.

A device for creating a capsulorhexis is needed that can be inserted through a standard corneal incision in a deformed configuration while having a rigidity such that it can be placed firmly onto the capsular bag. Described herein are such devices.

Disclosed herein are devices and methods for inserting a device through a narrow opening in a first configuration and then transitioning the device into a second configuration. The procedures disclosed herein include capsulorhexis procedures but also more broadly include all aspects of cataract surgeries, ocular surgeries, and any procedure where such a transition and insertion of a device through a small incision would be useful. Procedures include certain glaucoma surgeries, retinal surgeries, laparoscopic surgeries, robotic surgeries, colorectal surgeries, vascular surgeries, and the like.

A user for such a device may include physicians, surgeons, doctors, nurses, or anyone who would perform a procedure with such a device. In some embodiments, the devices described herein transition from a first configuration to a second configuration, where the first configuration is used while inserting the device through a narrow opening, and the second configuration is used during some part of the procedure. A first configuration may be a bent configuration where the cross-sectional dimensions of the device allow it to be passed through a narrow opening. A second configuration may be an unbent configuration where one or more cross-sectional dimensions of the device would not be able to pass through the narrow opening. The device may transition between the first configuration and second configuration through user manipulation, automatically, robotically, or otherwise. The user manipulation may occur outside the narrow opening. There may also exist transitional configurations between the first and second configuration.

Described herein are devices and methods for creating a capsulorhexis in an eye. The device may be a single-use disposable device or may include one or more reusable components and assemblies that are sterilized after use. In some embodiments a template is described which forms a tearing profile. The term 'template' may describe the element of the device that has the tearing profile or may describe the entire device and system. The term 'template' should not be limited to describing devices which include a tearing profile but may also include devices such as guides, calipers, indicators, displays, aides, and the like. In any of the embodiments described herein, the template may provide a visual reference of the size and shape of the capsulorhexis being created but may not necessarily include a tearing profile. In some embodiments, the template includes a sharp edge which can cut the capsulorhexis when a downward force is applied. In other embodiments, the template is an aperture for a light-based capsulotomy technique, such that the template covers the regions of the capsular bag which are not to be ablated. The term 'template' may refer to any and all devices which are used for aiding in the creation of a capsulorhexis or in any other aspect of ocular surgery.

In some embodiments, a template includes a first side having a tearing profile in contact with a capsular bag of a subject, and a second side opposite the first side. The tearing profile is configured to provide a perimeter or boundary edge for a torn capsulorhexis or capsulotomy. As the capsulorhexis or capsulotomy is created by a user, the tearing profile of the template guides the split in the capsular bag so that the resulting capsulorhexis or capsulotomy profile is similar to the shape of the tearing profile. In some embodiments, the template further includes one or more rigid sections with one or more gaps between the rigid sections which define bendable sections. The bendable sections may be bent during insertion of the template into the eye through a corneal incision representing a first configuration. The bendable sections may then be unbent once the template is at least partially within the eye representing a second configuration. The rigid sections of the template may be manipulated to transition the template between the first configuration and the second configuration. The bendable sections may divide the template into two or more regions or portions where the rigid sections are located. The portions may be of equal or unequal sizes. In some embodiments, there can be three or four portions or a plurality of portions defined by three or four or a plurality of rigid sections, respectively, that are separated by three or four or a plurality of bendable areas. In such embodiments, the template may bend across multiple bending axes.

As described herein, the terms 'rigid' and 'stiff' are intended to signify an area of a component which does not undergo substantial deformation during the intended use of the device, while the terms 'flexible', 'bendable', 'foldable', and 'elastic' are intended to signify an area of a component which may undergo substantial deformation and more specifically elastic deformation during the intended use of the device. In general, the methods may include inserting a template into an eye, depressing the template against the surface of the capsular bag, and tearing the capsular bag in a way that follows the tearing profile of the template.

Devices

The devices described herein function to assist in the creation of a capsulorhexis. In some embodiments, the devices function to place a template on the capsular bag of an eye that can be used to trace a capsulorhexis. The device is used for ocular surgery but may additionally or alternatively be used for any suitable applications, clinical or otherwise. The device may be configured and/or adapted to function for any suitable field where the insertion of large profile tools through a narrow opening is required.

FIG. 1 shows an embodiment of a device for creating a capsulorhexis. In some embodiments, as shown in FIG. 1, the device is a template 102 which includes a top surface or second side 108 and a bottom surface or first side 116 separated by a height 112, and an inner surface 106 and an outer surface 114 separated by a width 110. Along the bottom surface 116 of the template 102, in some embodiments, there is a tearing profile 104 that is continuous circumferentially. In other embodiments, the tearing profile 104 may be discontinuous, such that is punctures the capsular bag in one or more locations. In still other embodiments, as described elsewhere herein, the tearing profile 104 may be triangular, diamond-shaped, square-shaped, or any other shape. The template 102 has a width 110 and height 112 of its cross-sectional shape at any given location around its circumference. In some embodiments shown in FIG. 1, the width 110 is 0.1 mm to 0.5 mm and the height 112 is 0.5 mm to 1.5 mm. In some embodiments, the width 110 and height 112 are generally constant around the circumference as shown in FIG. 1. In other embodiments, the width 110 and height 112 may vary around the circumference such that different cross-sectional sizes exist around the perimeter.

Figure 2:
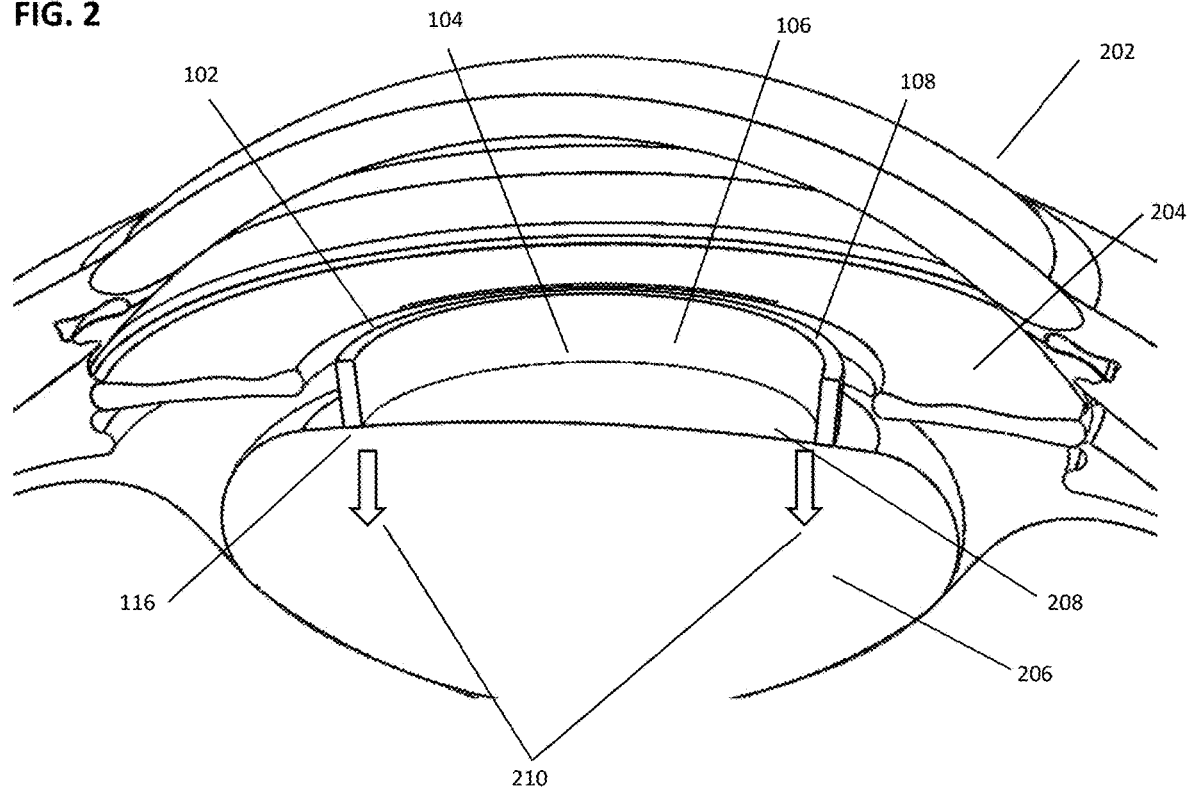
FIG. 2 illustrates the embodiment of FIG. 1 within an eye.
Figure 4:
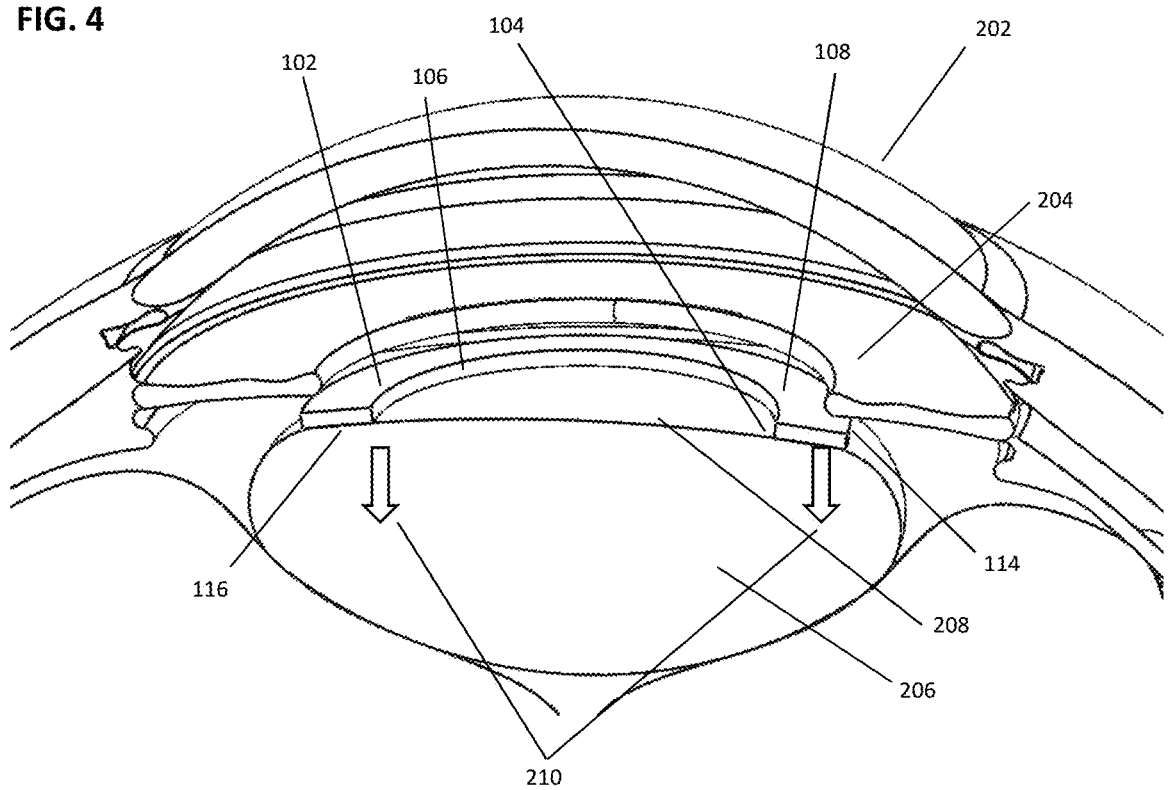
FIG. 4 illustrates the embodiment of FIG. 3 within an eye.

The tearing profile 104 is placed against the anterior surface of a capsular bag 208, as shown in FIG. 2. As shown in FIGS. 2 and 4, the eye includes a cornea 202, an iris 204, a lens 206, and a capsular bag 208 which surrounds the lens 206. In cataract surgery, a circular opening is made in the capsular bag 208 so that the lens 206 can be removed and replaced with an artificial lens. A small incision is made through the cornea 202 which is typically less than 3.0 mm and often 2.2 mm or less. The tearing profile 104 may be generally circular, although other shapes are contemplated herein, and have a diameter that is approximately the desired diameter of the capsulorhexis, or about 3-7 mm in diameter; in other embodiments, the diameter is 4-6 mm in diameter. A downward force 210 may be applied to the template 102 such that the tearing profile 104 remains in intimate contact with the capsular bag 208 while the capsulorhexis is being torn, as will be described in detail elsewhere herein.

As shown in FIG. 1, the height 112 of the template 102 is generally greater than the width 110 such that the template 102 resembles a ring with an outer surface 114 and inner surface 106 that are each greater than the bottom surface or first side 116 or the top surface or second side 108. In some embodiments, the inner surface 106 of the template 102 may be drafted or tapered outward (e.g., narrower at a point of contact with the capsular bag or broader at a point of contact with the capsular bag) to provide greater visualization and access to the user as they tear the capsulorhexis along the tearing profile 104.

Figure 3:
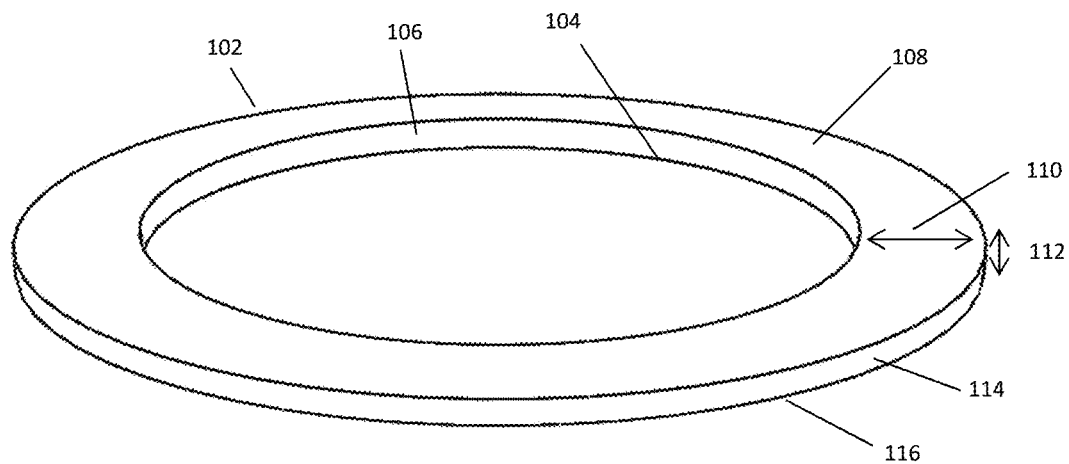
FIG. 3 illustrates an embodiment of a device for creating a capsulorhexis, the device having a generally flat profile.

FIG. 3 shows a template 102 with width 110 which is generally larger than the height 112 such that the template 102 resembles a disc that is generally planar. In some embodiments, for example as shown in FIG. 3, the width 110 is 0.5 mm to 1.5 mm, and the height is 0.1 mm to 0.5 mm. The device is shown placed against a capsular bag 208 in FIG. 4. with the tearing profile 102 defining a capsulorhexis shape that will be created when the user tears the capsular bag 208 material away. An advantage of a flatter disc shape shown in FIG. 3 and FIG. 4 is that it may further reduce the possibility of a tear extending past the outer surface 114 of the template.

Figure 5A:
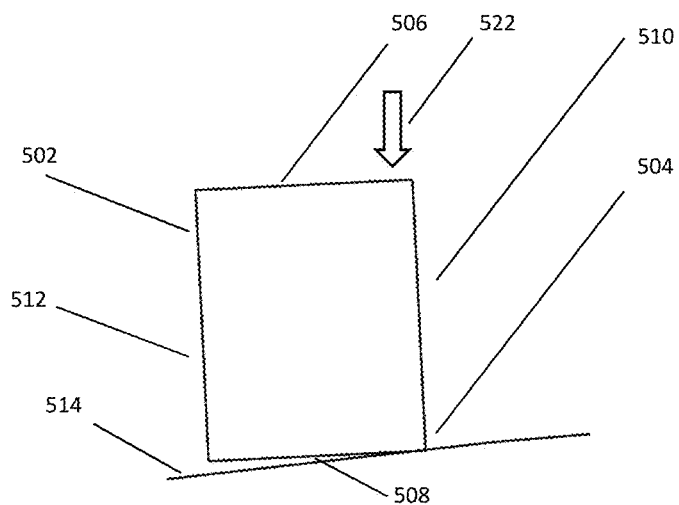
FIG. 5A illustrates a cross-sectional view of a device, with a tearing profile, for creating a capsulorhexis.
Figure 5B:
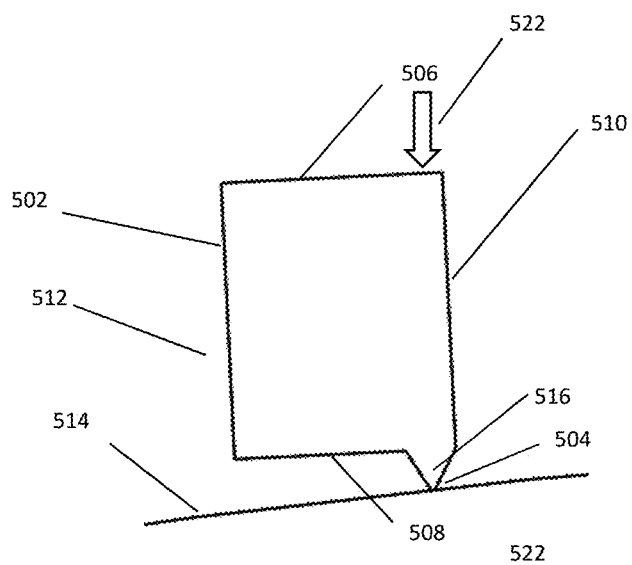
FIG. 5B illustrates a cross-sectional view of a device, with a tearing profile, for creating a capsulorhexis.
Figure 5C:
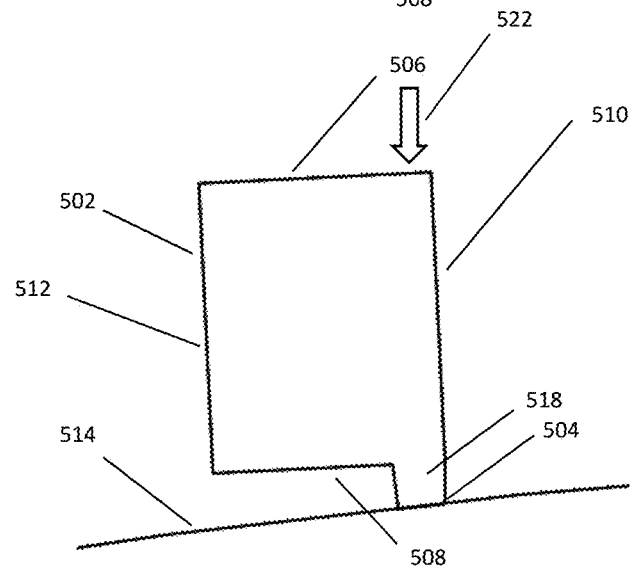
FIG. 5C illustrates a cross-sectional view of a device, with a tearing profile, for creating a capsulorhexis.
Figure 5D:
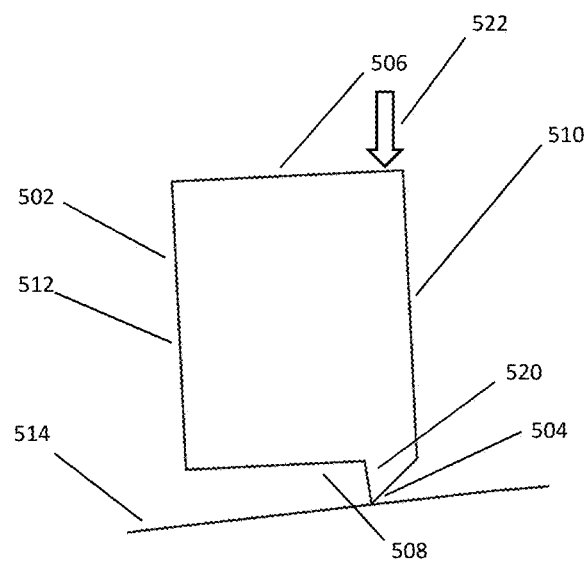
FIG. 5D illustrates a cross-sectional view of a device, with a tearing profile, for creating a capsulorhexis.
Figure 5E:
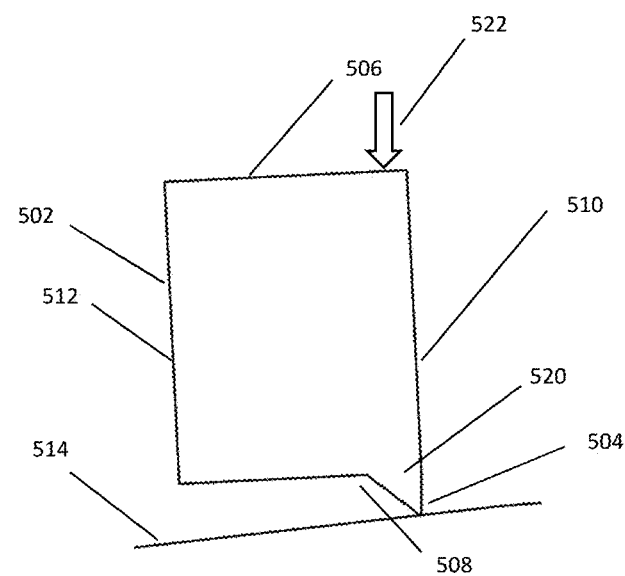
FIG. 5E illustrates a cross-sectional view of a device, with a tearing profile, for creating a capsulorhexis.

FIGS. 5A-E show various cross-sectional profiles of a template 502. The template includes a top surface or second side 506, a bottom surface or first side 508, an inner surface 510, and an outer surface 512. Along the bottom surface 508 of the template 502, there is a tearing profile 504. In some embodiments, as shown in FIG. 5A, the profile of the tearing profile may be a sharp corner. The corner may be 50 to 120 degrees in some embodiments and may be 70 to 100 degrees in other embodiments. The tearing profile 504 is placed in intimate contact with the capsular bag 514 during the capsulorhexis procedure with a downward force 522. As the surgeon tears the capsular bag 514 material, the tear will propagate up to the tearing profile 504 but will not extend past the tearing profile 504 and will instead continue to follow the tearing profile 504 around the perimeter of the inner surface 510 of the template 502 such that a capsulorhexis of a desired shape is created. As shown in FIGS. 5B-E, the template 502 further includes protrusions that extend from the bottom surface or first side 508 of the template 502. In some embodiments, as shown in FIG. 5B, the tearing profile 504 is defined by the point of a generally isosceles triangle protrusion 516. In other embodiments, as shown in FIG. 5C, the tearing profile 504 is defined by the inner corner of a small rectangular protrusion 518 on the bottom surface 508 of the template 502. As shown in FIG. 5D and FIG. 5E, the tearing profile 504 is defined by the point of generally right triangle protrusion 520 in different configurations. A potential benefit with using a tearing profile 504 which exists on a protrusion below the bottom surface 508 of the template 502, as shown in FIGS. 5B-E, is that the downward force 522 applied to the template onto the capsular bag 514 is spread across a smaller area and therefore may have a higher pressure than the tearing profile 504 shown in FIG. 5A. Such a feature may result in a reduced likelihood of the capsulorhexis tear extending beyond the tearing profile 504. The template 502 may include a single tearing profile 504 or may include multiple tearing profile 504 cross-sectional shapes such as a combination of any of the embodiments shown in FIGS. 5A-E or any other suitable shape. The tearing profile 504 may exist near the inner surface 510 of the template 502, as shown in FIGS. 5A-E, or may be located near the outer surface 512 of the template 502 or at any location therebetween.

In some embodiments, the template 502 may include one or more sharp corners and edges along the tearing profile 504. In these embodiments, the downward force 522 of the template 502 onto the capsular bag 514 may create some or all of the capsulorhexis by itself such that tearing of the capsular bag 514 may be reduced or obviated completely. For example, in FIG. 5B the isosceles triangle protrusion 516 which defines the tearing profile 504 may actually be a blade edge which is sufficiently sharp to cut the capsular bag when a downward force 522 is applied to the template 502. As will be discussed in greater detail elsewhere herein, some embodiments may include blade edges along the tearing profile 504 or anywhere along the bottom surface or first side 508 of the template 502.

Figure 6:
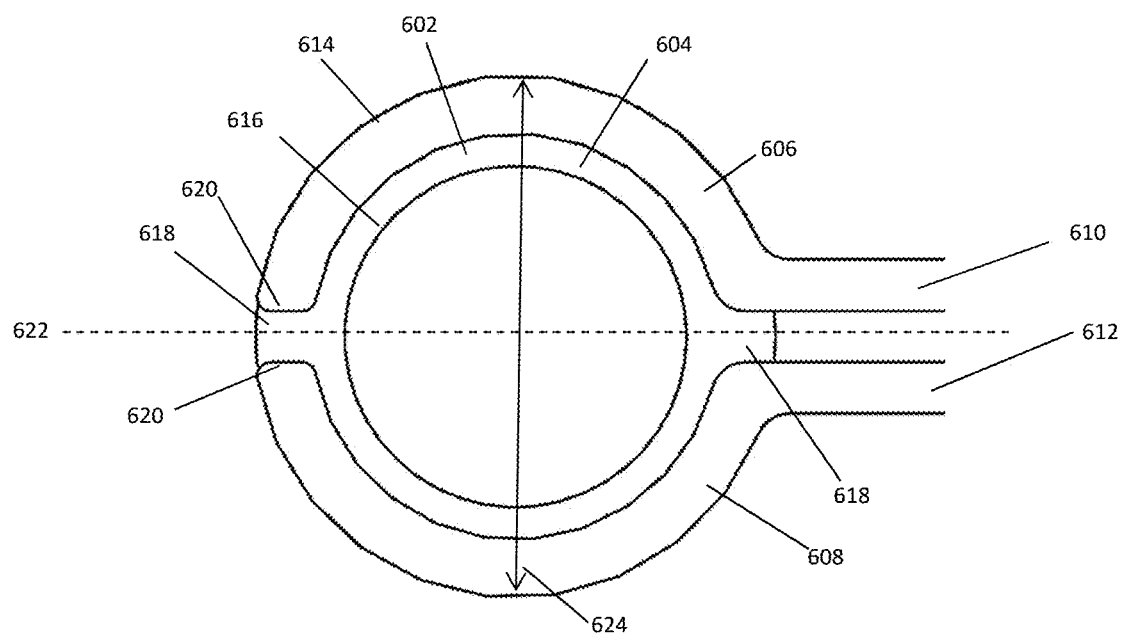
FIG. 6 illustrates a top view of an embodiment of a device, with template backers, for creating a capsulorhexis.

FIGS. 6-12 show an embodiment of a device which includes a template 602 which includes a bendable area 618. The template 602 is comprised of a top surface or second side 702, a bottom surface or first side 1004, an inner surface 616, and an outer surface 614. The template 602 has a template width 624 which is larger than a corneal incision, typically 3.0 mm. A tearing profile 604 exists on the bottom surface 1004. The tearing profile 604 may be near the inner surface 616 of the template 602 as shown in FIG. 6 or in other embodiments may be near the outer surface 614 or in still other embodiments may be in an location therebetween. The bendable area 618 may be a location on the template 602 that allows the device to be folded as shown in the subsequent figures. In some embodiments, as shown in FIGS. 6-12, the template 602 may include a plurality of components that together comprise the template 602. For example, as shown in FIG. 6, the template 602 may be an elastomeric flexible material such as a silicone, thermoplastic elastomer (TPE), nitinol, or polyurethane or any other suitable material. A right or first template backer 606 and a left or second template backer 608 are attached on one side of the template 602. The template backers 606, 608 may include or be formed of a stiffer material such as a stainless steel, nitinol, plastic, or any other suitable material. The template backers 606, 608 provide stiffness and rigidity to the template 602 such that it may be maneuvered within the eye and firmly held on top of the capsular bag. Without template backers 606, 608, the template 602 may be insufficiently rigid for the intended purposes of the device. The template 602 by itself, if made of a flexible material, may be difficult to manipulate in the eye. For example, transitioning the template 602 between a first bent configuration (e.g., FIGS. 10-11) and a second unbent configuration (e.g., FIGS. 6-7) may not be possible without one or more rigid sections. In the embodiments show in FIGS. 6-12, the right template backer 606 and left template backer 608 create rigid sections on the template 602 that allows the template 602 to be transitioned between bent and unbent configurations by manipulation of the template backers 606, 608. Furthermore, without rigid sections on the template 602, applying a downward force 1206 on the template 602 may not result in intimate contact of the template 602 against the capsular bag around the entire perimeter of the tearing profile 604.

The template backers 606, 608 support the template 602 and provide several key functions. The template backers 606, 608 allow the device to be manipulated within the eye such that the template 602 may be positioned correctly over the optic axis. Further, the template backers 606, 608 allow the template 602 to be pressed against the capsular bag with a more distributed pressure when a downward force 1206 is applied such that the entire perimeter of the tearing profile 604 is in intimate contact with the capsular bag. Lastly, the template backers 606, 608 also allow the template 602 to be transitioned between a first bent configuration and a second unbent configuration through manipulation of the template backers 606, 608, as will be described in greater detail elsewhere herein. The template backers define a rigid section of the template 602. The rigid section may still deform during use, but it is intended to be stiffer than the bendable area 618 of the template 602 such that when the template backers are rotated relative to one another, they bendable area 618 substantially bends whereas the template backers do not. Substantial bending may be considered more than 40 degrees of bending in some embodiments or more than 10 degrees of bending in some embodiments or more than 3 degrees of bending in still other embodiments.

In some embodiments, the template backers 606, 608 have an area, for example a linker region 618, where they are not connected or not continuous which forms a bendable area 618 on the template 602. In other words, the linker region 618 comprises the bendable area 618 of the template 602. In such an area, the template 602 may bend and fold if the template backers 606, 608 are rotated. The linker region or bendable area 618 may bifurcate the template 602 into two portions. For example, as shown in FIG. 6, the first portion may be the left side of the device between the two bendable areas 618 where the left template backer 608 is on the template 602. Similarly, for example, the second portion may be the right side of the device between the two bendable areas 618 where the right template backer 606 is on the template 602. As shown in FIG. 6, two bendable areas 618 are shown, but any other number of bendable areas 618 may also be considered. For example, the template 602 may be folded along multiple planes such that the template 602 resembles a quarter or eighth segment of a circle.

The two bendable areas 618, as shown in FIG. 6, exist along a bending axis 622. The bending axis 622 is the approximate axis which the template 602 is folded and unfolded about. The template backers 606, 608 have a right or first connector 610 and left or second connector 612 that extend from one end of the template 602. The connectors 610, 612 function to provide the user with control over the device. In some embodiments, the connectors 610, 612 extend through the corneal incision such that the user may move or manipulate a device which is inside the eye from outside the eye. The connectors 610, 612 may be coupled to or a part of the template backers 606, 608 and, therefore, as the connectors 610, 612 are moved, the device may be moved and manipulated. For example, moving the connectors 610, 612 together may cause the template backers 606, 608 and template 602 to move accordingly within the eye. The connectors 610, 612 may also be used to place a downward force from the template 602 onto the capsular bag during the capsulorhexis procedure. The connectors 610, 612 may also be rotated relative to one another such that the template 602 transitions from a first bent configuration to a second unbent configuration.

Figure 7:
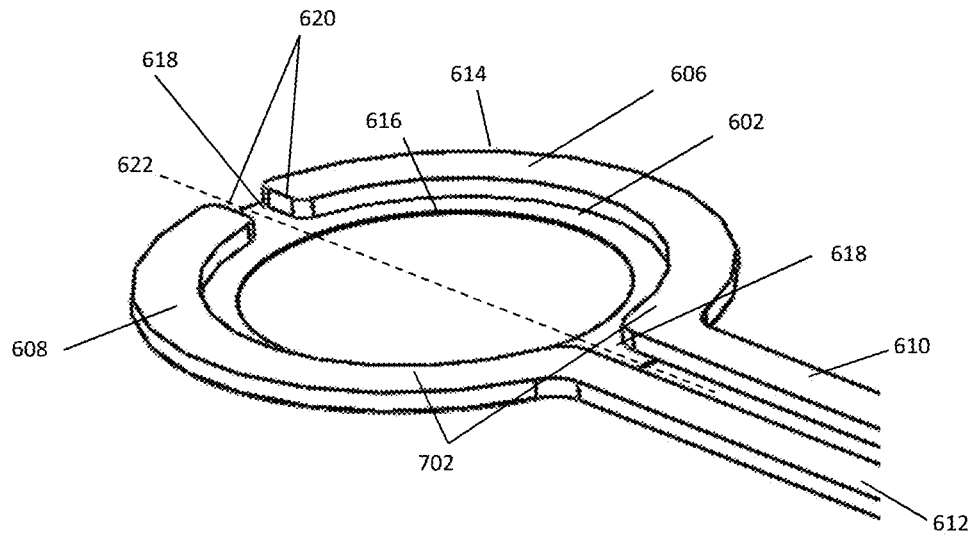
FIG. 7 illustrates an isometric view of the embodiment of FIG. 6.

In some embodiments where the connectors 610, 612 extend through a corneal incision, the user is able to manipulate the template 602 which is within the eye from outside the eye. Such an embodiment is particularly useful for transitioning the template 602 back into a first configuration after the capsulorhexis creation in order to remove the device from the eye. The connectors 610, 612 may be separate elements that are connected to the template backers 606, 608 or may be a feature of the template backers 606, 608, as is shown in FIG. 6. When the template 602 is placed on a capsular bag, the connectors 610, 612 may extend through the corneal incision such that the user may manipulate the position and shape of the template 602 from outside the eye. For example, the user may apply a downward force on the connectors 610, 612 such that the template 602 and tearing profile are firmly placed against the capsular bag. The connectors 610, 612 may also control the shape of the template 602. As shown in FIG. 7, the template 602 is in a second configuration with the tearing profile in an unbent configuration that may be used to form a stencil for a capsulorhexis. As will be shown, the connectors 610, 612 and template backers 606, 608 may be rotated to cause the template 602 to transition into other configurations.

In some embodiments, the template backers 606, 608 are intended to support the template 602 and make the combined assembly more rigid. In some embodiments, the template backer 606, 608 may be a discrete layer on the top surface 702 of the template 602. In other embodiments, the template backers 606, 608 may be a discrete layer in the middle of the template 602 or on the bottom surface 1004 of the template 602. In some embodiments, the template backers 606, 608 may be a flat piece of sheet metal. In other embodiments, the template backers 606, 608 may be a wire, a tube, or any other suitable structure.

The template backers 606, 608 may be connected to the template 602 by any number of standard manufacturing methods such as adhesives, overmolding, thermoforming, heat staking, ultrasonic welding, laser welding, mechanical fastening, or the like.

In various embodiments, the template backers 606, 608 may be considered rigid or stiff in the area where they support the template 602 over the tearing profile 604. In some embodiments, the template backers 606, 608 include one or more of: metal, nitinol, polymers, or any other suitable material. In some embodiments, the template backers 606, 608 may include a metal with a modulus of elasticity of 150 GPa to 200 GPa, 170 GPa to 190 GPa, or any range or subrange therebetween. In some embodiments, the template backers 606, 608 may include nitinol with a modulus of elasticity of 25 GPa to 80 GPa, 40 GPa to 60 GPa, or any range or subrange therebetween. In some embodiments, the template backers 606, 608 may include a polymer with a modulus of elasticity of 1.0 GPa to 3.5 GPa, 2.0 GPa to 3.0 GPa, or any range or subrange therebetween.

The template 602 may be flexible or bendable and may include silicone or TPE with a modulus of elasticity in the range of 0.01 GPa to 0.5 GPa, 0.1 GPA to 0.2 GPa, or any range or subrange therebetween. In some embodiments, the template 602 has a hardness of 30 Shore A to 90 Shore A, 50 Shore A to 70 Shore A, or any range or subrange therebetween. Therefore, when the template backers 606, 608 are rotated, they are generally stiffer than the template 602 and hence the template 602 bends in the bendable areas 618 where the template backers 606, 608 do not exist. While the template backers 606, 608 are generally more rigid than the template 602, they may still deform when placed on the capsular bag. However, they are configured to impart a sufficient downward force 1206 against the surface of the capsular bag which may be in the range of 0.2 N to 10 N. In other embodiments, the template backers 606, 608 are configured to impart 0.5 N to 2.0 N of downward force 1206 against the surface of the capsular bag. Further, in some embodiments, the template backers 606, 608 are configured to provide sufficient downward force 1206 to the flexible template 602 such that they may bend and unbend the template 602 as needed. Further, as will be disclosed in greater detail elsewhere herein, the template backers 606, 608 may flex and deform in a flexible area 1202 which may provide a downward force 1206 on the capsular bag.

Figure 8:
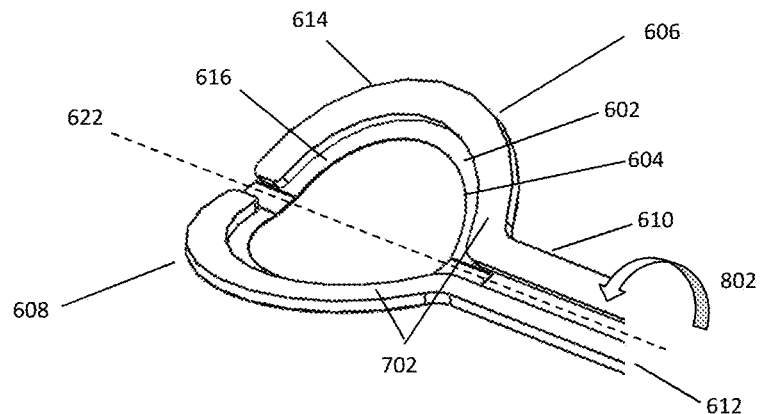
FIG. 8 illustrates an isometric view of the embodiment of FIG. 6 with the device slightly bent or folded about a bending axis.
Figure 9:
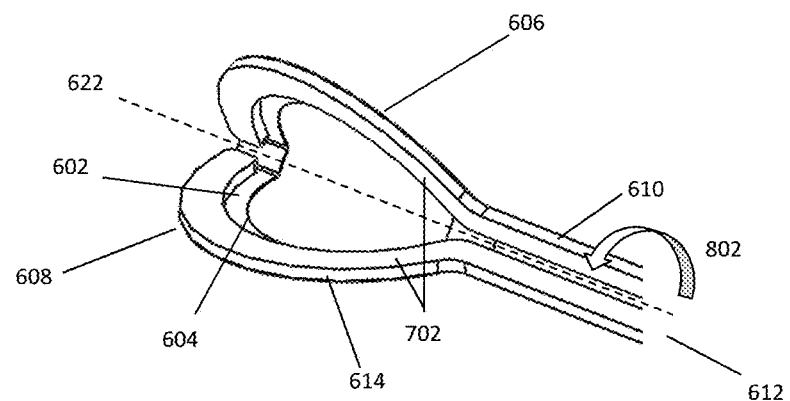
FIG. 9 illustrates an isometric view of the embodiment of FIG. 6 with the device partially bent or folded about a bending axis.

As shown in FIG. 8, the right template backer 606 is rotated with a torque 802 such that it starts to fold over slightly onto the left template backer 608. Since the template backers are relatively stiff compared to the template 602, they may rotate and bend the template 602 at or near the bendable area 618 where the template backers do not connect. As shown in FIG. 9, the template 602 is shown bent further or partially as compared to FIG. 8 with further application of a torque 802, and in FIG. 10, the template is shown mostly bent into a compact shape that resembles a half circle. One of the bendable areas 618 has formed an entry surface 1002 on the bottom surface 1004 of the template where the template 602 may be inserted through a corneal incision. During the transition between the unbent configuration shown in FIG. 7 and the bent configuration shown in FIG. 10, the top surface 702 and the right template backer 606 and the top surface 702 and the left template backer 608 have become closer. There exists an angle between the two top surfaces 702 or between the two template backers 606, 608 that changes between the configurations. The first bent configuration shown in FIG. 10 may have an angle between the right template backer 606 and the left template backer 608 of −20 to 20 degrees or, in other embodiments, −5 to 5 degrees. The second unbent configuration, as shown in FIG. 7, may have an angle between the right template backer 606 and the left template backer 608 of 150 to 210 degrees or, in some embodiments, 175 to 185 degrees. In the first bent configuration shown in FIG. 10, the distance between the two top surfaces 702 over the template backers 606, 608 is reduced to an adjacent or proximate state which is less than 1.0 mm in some embodiments or less than 0.25 mm in other embodiments. In still other embodiments, the two top surfaces 702 may be in intimate contact. In some embodiments, the top surfaces 702 may be adjacent in some areas only. For example, the top surfaces 702 may be adjacent the cross-section location where the template crosses the corneal incision but the distance between the top surfaces 702 may be simultaneously further away in other areas. The adjacent top surfaces 702 defines a folding of the template into a first bent configuration.

Figure 10:
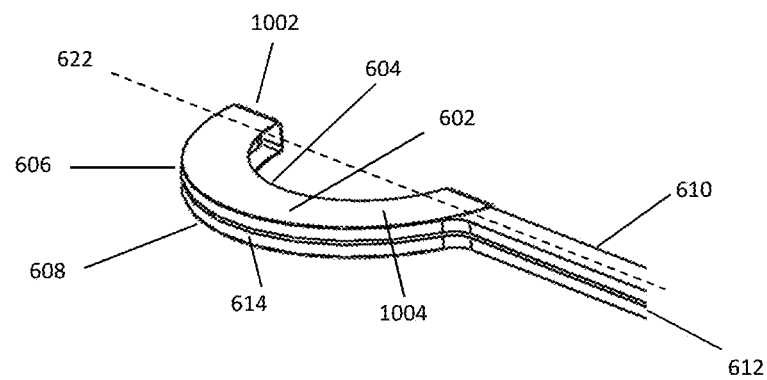
FIG. 10 illustrates an isometric view of the embodiment of FIG. 6 with the device mostly bent or folded about a bending axis.
Figure 11:
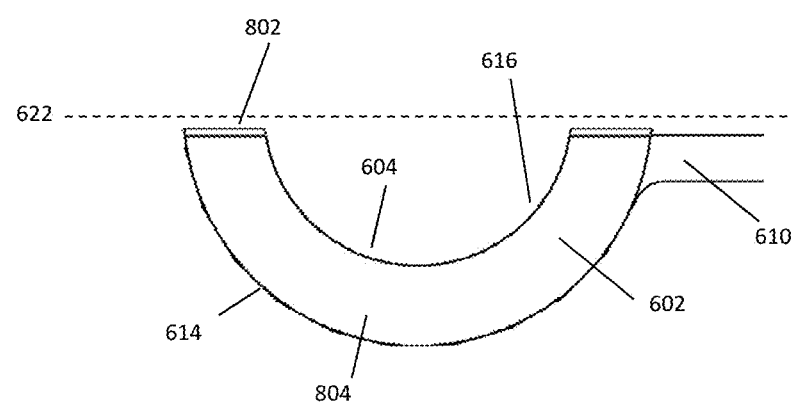
FIG. 11 illustrates a top view of the embodiment of FIG. 10.

FIG. 11 shows a top view of a mostly bent template 602 as shown in FIG. 10. In such a configuration, the device may be inserted through a small incision in the eye such as a clear conical incision, for example less than 3.0 mm. In other embodiments, the incision in the eye is less than 2.2 mm. The template 602 is hooked into the incision such that it enters the anterior chamber. Once the template 602 is inside of the anterior chamber, the template backers may be rotated so they open up and are configured as shown in FIG. 7. The template 602 may be maneuvered over the top of the capsular bag and placed down on the capsule. The user may apply sufficient downward force 1206 on the capsule so the template 602 is held intimately against the surface of the bag and may form the capsulorhexis profile and define the boundary of the desired capsulorhexis.

The device shown in FIG. 10 defines a first bent configuration that is used during insertion of the device through the corneal incision into the eye. The first bent configuration has a cross sectional area as it crosses the corneal incision. The cross-sectional area may be between 0.75 mm$^2$ and 3.0 mm$^2$ such that the device may fit through a corneal incision that is less than about 3.0 mm, 2.8 mm, 2.6 mm, 2.4 mm, 2.2 mm, 2.0 mm, or an incision of any size.

FIGS. 7 and 10-11 show the complexities of inserting an unfolded device through an incision versus a fully or partially folded device. Exemplary bent configurations are shown in FIGS. 10-11. As shown in FIGS. 10-11, the shape of the template 602 is roughly a half-circle shape with the height defined by the double the thickness of the template 602 and template backer. The shape shown in FIGS. 10-11 may be inserted through a relatively small corneal incision. An exemplary unbent configuration is shown in FIG. 7. As shown in FIG. 7, in some embodiments, the unbent shape is roughly a full circular profile that defines the boundaries of a capsulorhexis. The unbent configuration could not be directly inserted through a conical incision because its width is at least as wide as the diameter of the capsulorhexis. For example, if the capsulorhexis is approximately 5.0 mm diameter, then the width of the device may be 7.5 mm since each edge of the template 602 may be approximately 1.25 mm wide. Therefore, the device cannot be inserted through an incision that is less than 3.0 mm. However, if the device is folded into the configuration shown in FIG. 10-11, then it may be inserted through the corneal incision. Once inside the eye and with only the right connector 610 and left connector 612 extending through the corneal incision, the device may be unfolded to the second or unbent configuration and used during the capsulorhexis creation.

Figure 32A:
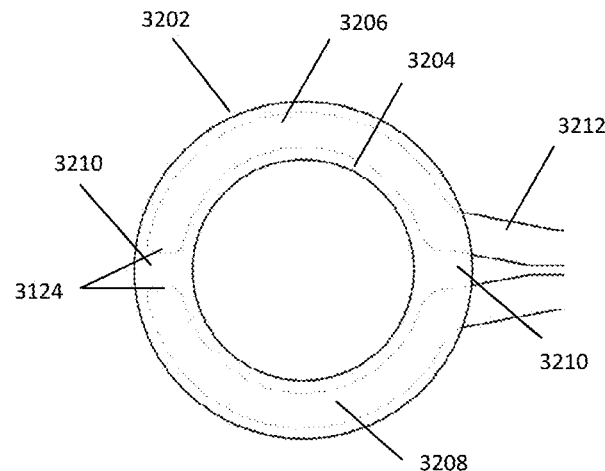
FIG. 32A illustrates a device for creating a capsulorhexis with a circular profile.
Figure 32B:
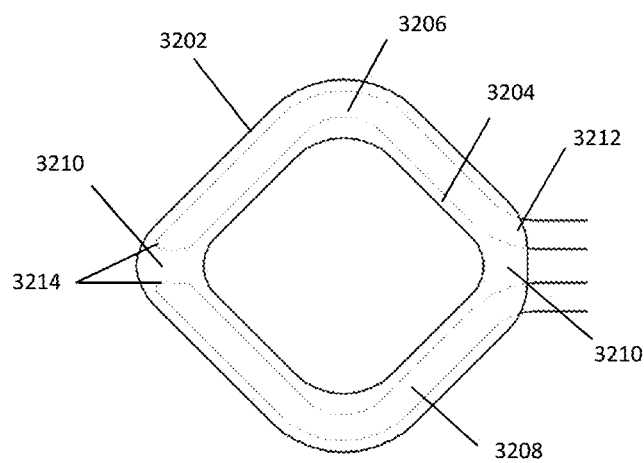
FIG. 32B illustrates a device for creating a capsulorhexis with a diamond profile.
Figure 32C:
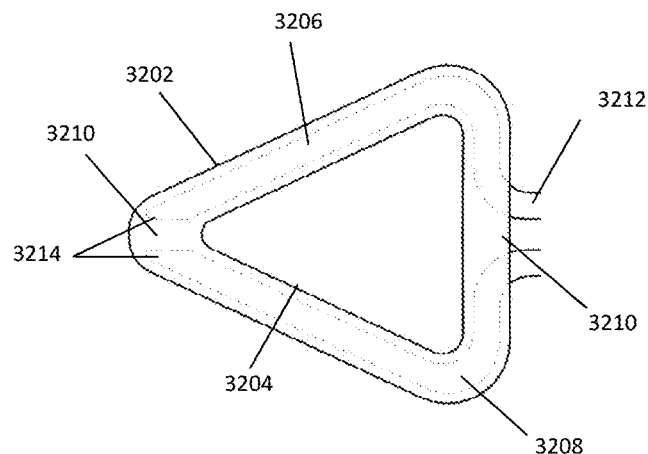
FIG. 32C illustrates a device for creating a capsulorhexis with a triangular profile.

When the device is unbent into the second configuration that is placed on the capsular bag, the tearing profile 604 of the template 602 forms a perimeter that defines the capsulorhexis to be created. The perimeter defined by the tearing profile 604 may be generally circle with a diameter of between 3 mm to 7 mm, 4 mm to 6 mm, 5 mm to 5.5 mm, or any range or subrange therebetween. Alternatively, the perimeter may be a non-circular shape such as an oval or ellipse. The perimeter may be any number of other shapes. In FIGS. 32A-C various tearing profiles 3204 are shown. A template 3202 with a right template backer 3206 and a left template backer 3208 which further includes template backer ends 3214 which define a bendable area 3210 is shown. The template 3202 further includes a flexible area 3212. The tearing profile 3204 of the template 3202 shown in FIG. 32A is a generally circular shape. In FIG. 32B, the tearing profile 3204 is generally a diamond, square, or rectangular shape. In FIG. 32C, the tearing profile 3204 is generally a triangle shape. Any number of other shapes or profiles are contemplated.

Figure 12:
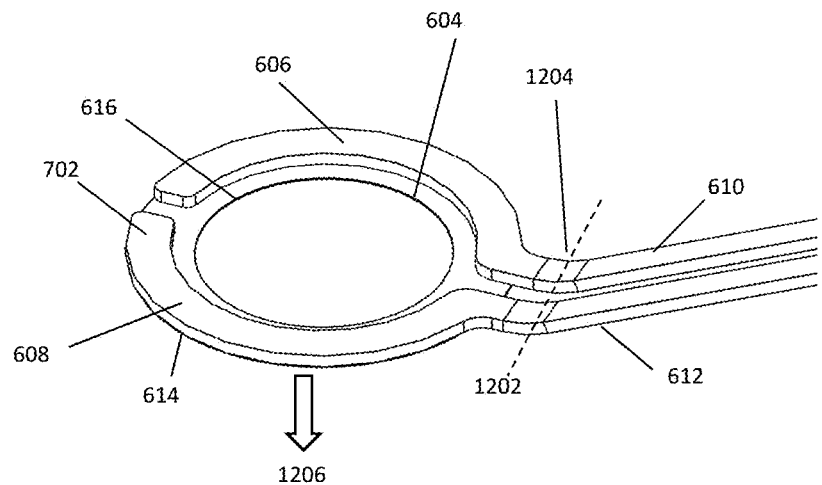
FIG. 12 illustrates an isometric view of the embodiment of FIG. 6 with the backers flexed.

Returning to FIG. 12, the template backers 606, 608 are shown in a flexed state. The anterior surface of the capsular bag tends to be more posterior in the eye than the corneal incision. Therefore, the right connector 610 and left connector 612 of the right template backer 606 and left template backer 608 may need to accommodate a change in angles. As shown in FIG. 12, a flexible area 1204 is shown where the connectors or template backers may flex about a flexing axis 1202. For clarification, the terms flexing, bending, folding, and hinging may be used interchangeably. As described herein, the term flexing has been used for the area where the connectors or template backers bend only for clarity. Any number of other terms may be used such as bending, folding, rotating, pivoting, deforming, or twisting. In one embodiment, the template backers 606, 608 may include or be formed of a material or thickness which allows them to be flexed elastically to such a configuration as shown in FIG. 12. For example, the template backers 606, 608 may include or be formed of nitinol which may be bent to such a shape without elastically deforming. Alternatively, a stainless steel or rigid plastic may be used which allows the template to be flexed in the flexible area 1204.

Figure 34A:
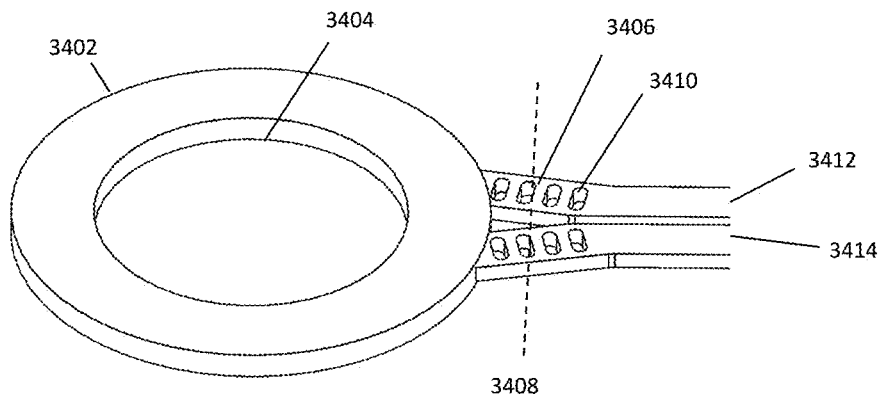
FIG. 34A illustrates a device for creating a capsulorhexis with a flexible area defined by cutouts.
Figure 34B:
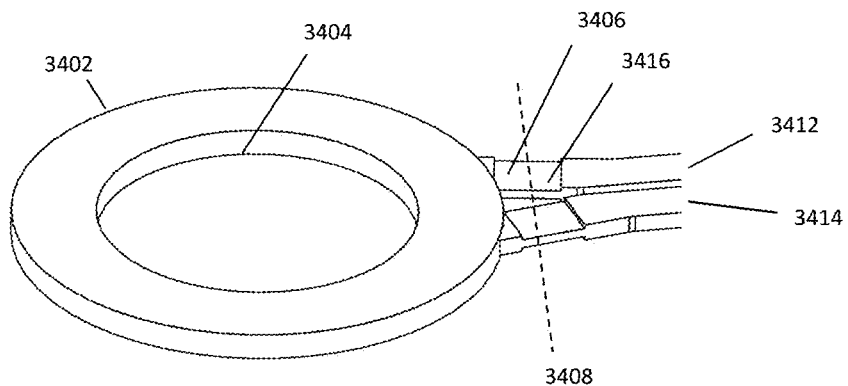
FIG. 34B illustrates a device for creating a capsulorhexis with a flexible area defined by a thin area.

FIGS. 34A-B show alternate embodiments of the flexible area 3406. A template 3402 is shown with a tearing profile 3404, a right connector 3412, and a left connector 3414. In FIG. 34B, the flexible area 3406 which bends about a flexing axis 3408 may be comprised of a material that has been locally thinned in the thin section 3416 to create a specific region designed to flex. For example, the template backers may be formed from stainless steel sheet metal with a nominal thickness in the range of 0.004 in to 0.020 in. The flexible area 3406 may have a local section with a thickness that is 20-80% of the nominal thickness which is therefore inherently more flexible. Such a flexible area 3406 may be created through chemical etching, laser cutting, machining, or any other suitable manufacturing process. In an alternate embodiment shown in FIG. 34A, the flexible area 3406 may be defined by one or more cutouts 3410 in the flexible area 3406 such that the material is not as stiff in the flexible area 3406. For example, a series of slotted cutouts 3410 through the thickness of the template backers and connectors in the flexible area 3406 may cause the material to flex easier. Alternatively, the flexible area 3406 may be a separate piece or material which is connected to the template backer and connector. For example, plastic or nitinol may be used for the flexible area 3406. Alternatively, a thinner stainless steel may define the flexible area 3406. Any number of other methods may be used to create a flexible area 3406. In some embodiments, the flexible area 3406 is locally stiffer than the template backers such that a higher downward force is imparted on the capsular bag.

Returning to FIG. 12, the flexible area 1204 allows for the device to accommodate an angle change from the approach angle of the incision to the location of the anterior portion of the capsular bag. The flexible area 1204 also may allow the user to place a gentle downward force 1206 onto the capsule. For example, if the template backer includes sufficiently thin nitinol material in the flexible area 1204, the amount of downward force 1206 that the user places onto the anterior portion of the capsular bag may be defined by the force required to bend the flexible area such that the template 602 is resting flat on the surface of the capsule. The device may be designed such that the downward force 1206 applied to the capsular bag is predetermined in a range which does not damage the ocular structures or does not exceed a certain maximum value which would cause clinical complications.

In other embodiments, that template 602 or template backers may include a shape memory material such as a nitinol. Such an embodiment may have certain advantages in the procedure. For example, the template backer may have a predefined bend programmed into the shape memory nitinol at a location near where the bendable area 618 is shown in FIG. 12. In such an embodiment, the device may enter the eye in a flat configuration without a bend in the template backer. Once the template backer equilibrates to the temperature of the ocular tissue after being inserted, it may exceed the predetermined transition temperature and form the bent configuration shown in FIG. 12. Such a shape memory change may reduce the force placed onto the capsular bag by the template 602 and the downward force 1206 may additionally be more uniform around the tearing profile 604. In other embodiments, the template 602 itself may include or be formed of a shape memory material such as nitinol. In such embodiments, the template 602 may be folded outside of the eye into a configuration shown in FIG. 11. Once inside the eye and equilibrated to the ocular temperature, the template 602 may unfold into the configuration shown in FIG. 7. Such a shape memory material may beneficially require less force to bend the template 602 into the bent configuration while inserting it into the eye.

In some embodiments, one of the template backers, such as the left template backer 608, remains stationary while the other template backer, such as the right template backer 606 is rotated 150 to 210 degrees or 175 to 185 degrees in some embodiments. Alternatively, both the right template backer 606 and left template backer 608 may be rotated 75 to 115 degrees or 85 to 95 degrees in some embodiments such that they meet in the middle or substantially in the middle.

Figure 13:
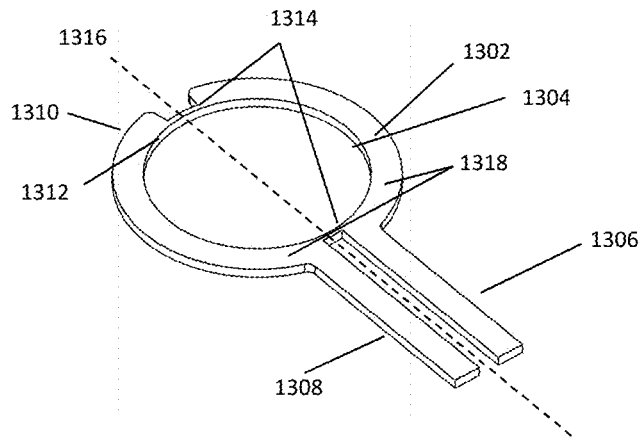
FIG. 13 illustrates an isometric view of an embodiment of a device, with a bendable area, for creating a capsulorhexis.
Figure 14:
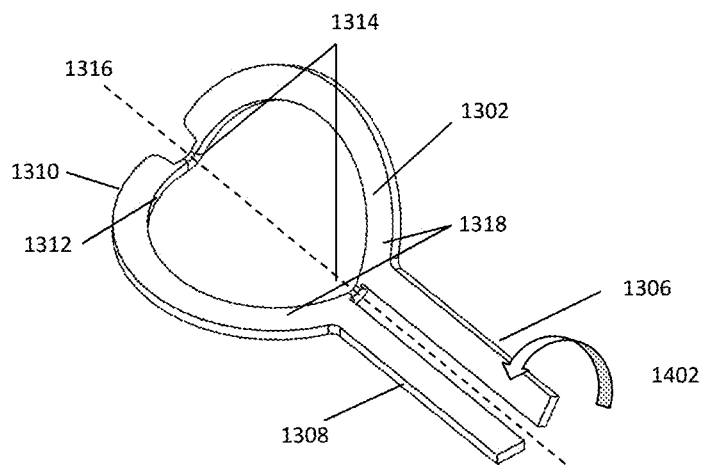
FIG. 14 illustrates an isometric view of the embodiment of FIG. 13 with the device partially bent or folded about a bending axis.
Figure 15:
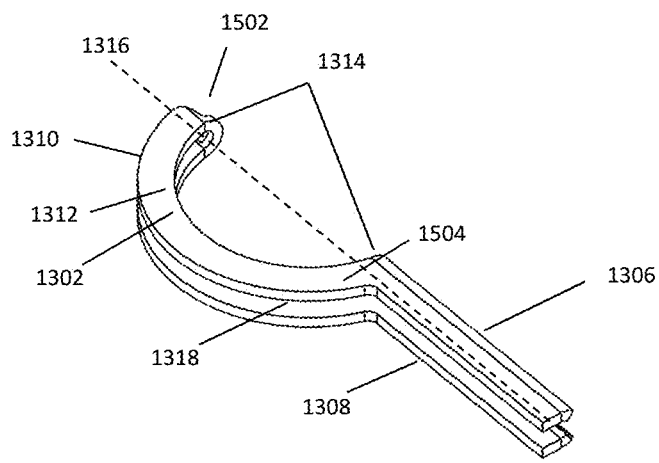
FIG. 15 illustrates an isometric view of the embodiment of FIG. 13 with the device fully bent or folded.

There are a variety of other embodiments that exist to create a template with a bendable area. For example, FIG. 13 shows an embodiment of a template 1302 including a single continuous inner surface 1312 which defines a tearing profile 1304. The template 1302 further includes a right connector 1306, a left connector 1308, an outer surface 1310, a top surface 1318, and one or more bendable areas 1314 which are configured to bend about a bending axis 1316. The bendable areas 1314, as shown in FIG. 13, are thin struts that allow the device to be bent with the right connector 1306 and left connector 1308 which are extending from the template 1302. In some embodiments, the template 1302 includes a first curved semicircular wall joined or coupled to a second curved semicircular wall via a strut region which defines an inner surface 1312. In some embodiments, the strut region is thinner than the first wall and/or the second wall. The connectors allow the user to bend and unbend the template 1302 to maneuver the device into and out of the eye through the incision. The connectors are rotated together and the device may be inserted into the incision in a configuration similar to what is shown in FIG. 15. As shown in FIG. 15, the template 1302 has an entry surface 1502 and a bottom surface 1504. Once the device is inside the anterior chamber, the device may be unfolded to the configuration shown in FIG. 13. The template forms a tearing profile 1304 along the inside surface 1312 of the template 1302. In the embodiment shown in FIG. 13, the user may use the connectors 1306, 1308 to apply a downward pressure onto the capsule so that the tearing profile 1304 maintains close contact with the capsular bag. As the bag is torn by the user, the tears should not extend beyond the tearing profile 1304 and should instead follow the tearing profile 1304 to form a circular capsulorhexis, as described elsewhere herein. Once the capsulorhexis is created, the user may further apply a torque 1402 to the right connector 1306 to fold the device into a transitional configuration shown in FIG. 14. The device is then further folded into the bent configuration shown in FIG. 15 and the device may be removed from the eye.

Figure 16:
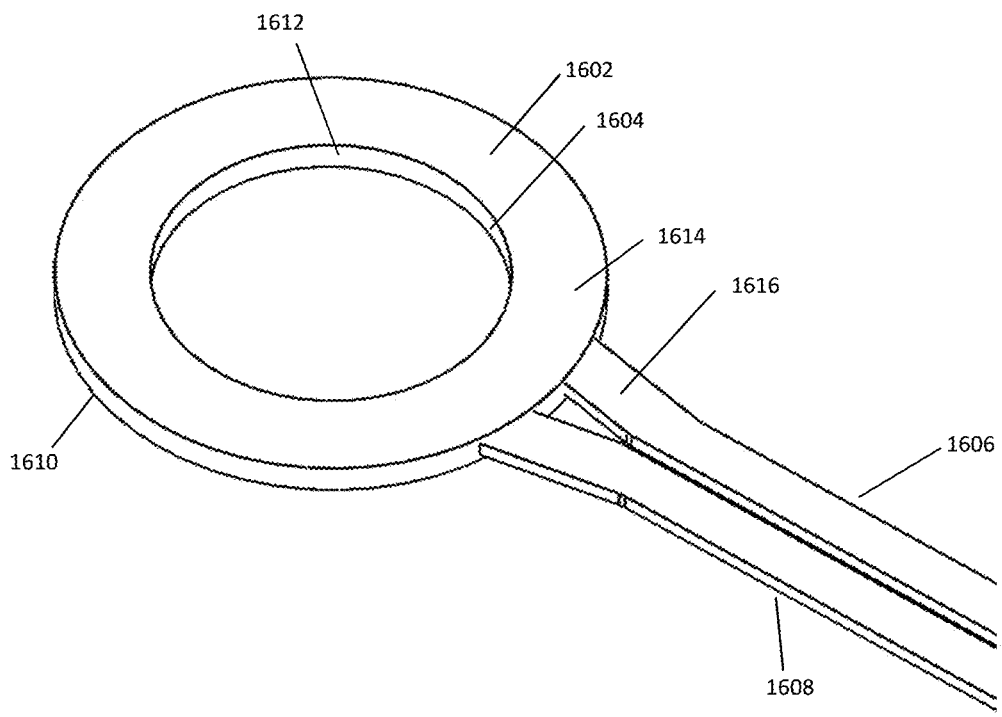
FIG. 16 illustrates an isometric view of an embodiment of a device for creating a capsulorhexis.

As shown in FIGS. 16-20, various configurations of an embodiment of a device for creating a capsulorhexis are shown. As shown in FIG. 16, a template 1602 is defined by a disc of flexible material such as silicone or TPE. The template includes an outer surface 1610, an inner surface 1612, and a top surface 1614. The device further includes a right connector 1604 and a left connector 1606. A tearing profile 1604 exists on a perimeter on the bottom surface 1904 of the template 1602. Inside the template 1602 are template backers which provide rigidity to the template 1602 according to their location and allow the template 1602 to be bent and unbent by rotating the template backers and connectors.

Figure 17:
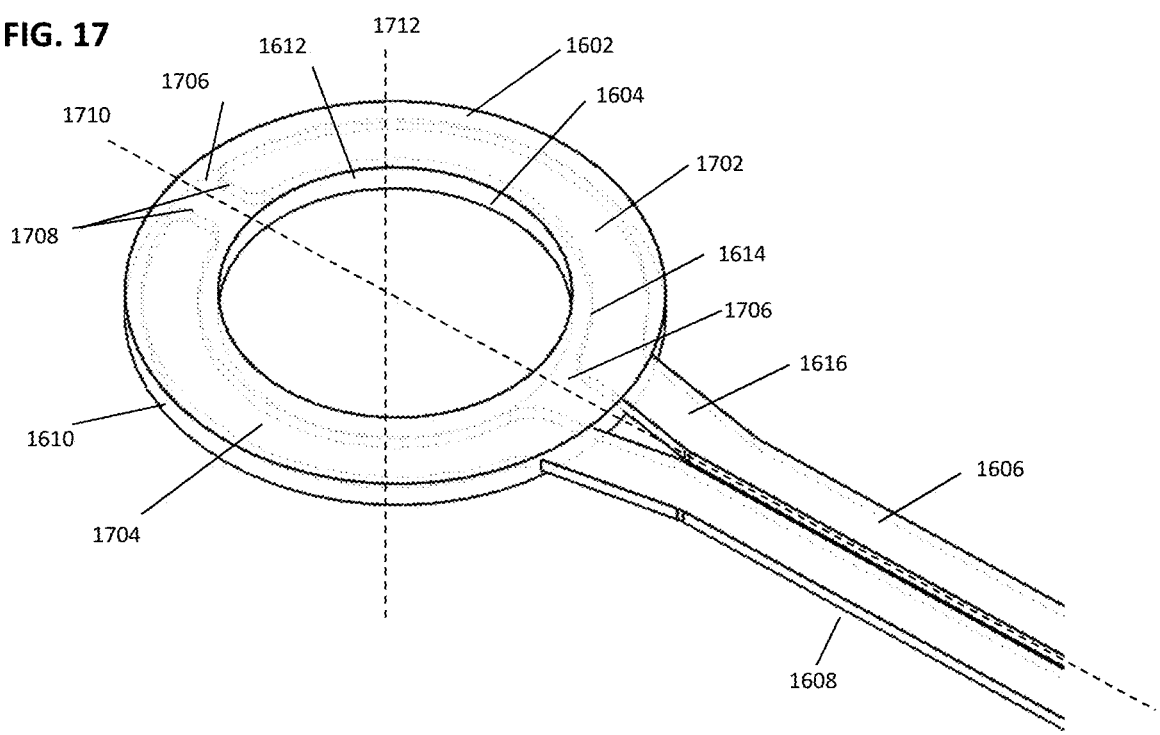
FIG. 17 illustrates a perspective view of the embodiment of FIG. 16 with the device partially transparent showing the template backers.

As shown in FIG. 17, a right template backer 1702 and left template backer 1704 are shown within the template 1602. The template 1602 may be over molded or cast over the template backers 1702, 1704. For example, the template 1602 may include or be formed of silicone which is liquid silicone resin molded or compression molded over the template backers 1702, 1704. Alternatively, the template backers 1702, 1704 may be inserted into a cavity within the template 1602. For example, the template 1602 may have a channel along its bottom surface 1904 that the template backers 1702, 1704 may fit into. The template 1602 and template backers 1702, 1704 may be connected using any number of methods such as adhesives, thermoforming, over molding, UV bonding, ultrasonic welding, or any other suitable method. The right connector 1606 and left connector 1608 may include one or more flexible areas 1616.

FIG. 17 further shows a central axis 1712 of the device. This may be the center of the tearing profile 1604. For example, the central axis 1712 may be defined by an axis extending from the center point of a circular tearing profile 1604. When in use, the central axis 1712 may be aligned with the optic axis of the eye such that the capsulorhexis is centered about the optic axis which is considered optimal for post-surgical outcomes.

Figure 18:
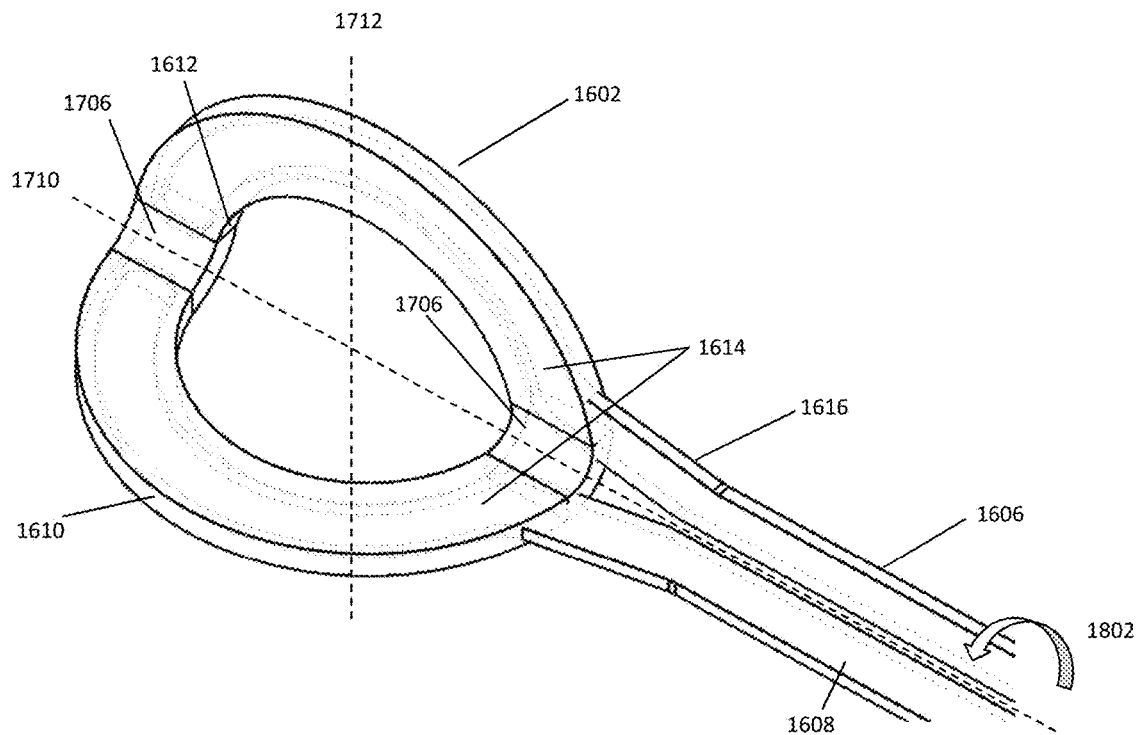
FIG. 18 illustrates a perspective view of the embodiment of FIG. 16 with the device partially bent or folded about a bending axis.
Figure 19:
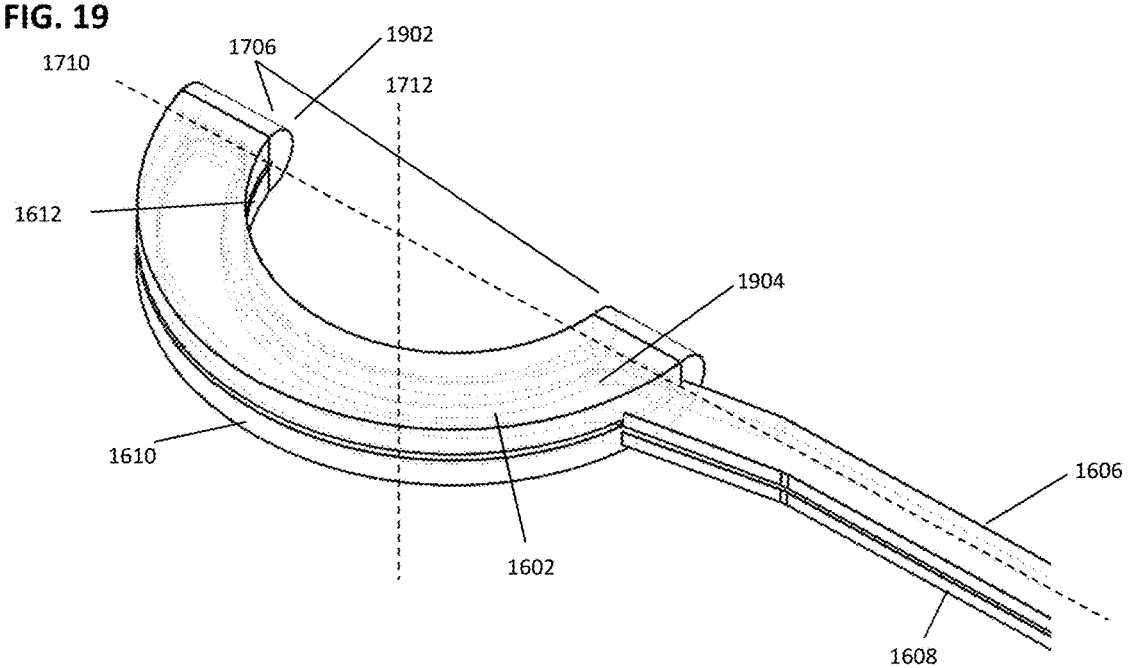
FIG. 19 illustrates a perspective view of the embodiment of FIG. 16 with the device mostly bent.

As shown in FIG. 18, the template backers are rotated with a torque 1802 such that the template 1602 begins to bend about a bending axis 1710 in the bendable areas 1706. The bendable areas 1706 may exist in the space between the template backer ends 1708 (shown in FIG. 17). As shown in FIG. 19, the template 1602 is fully bent such that the template 1602 is folded onto itself. The template 1602 may now be inserted into the eye.

Figure 20:
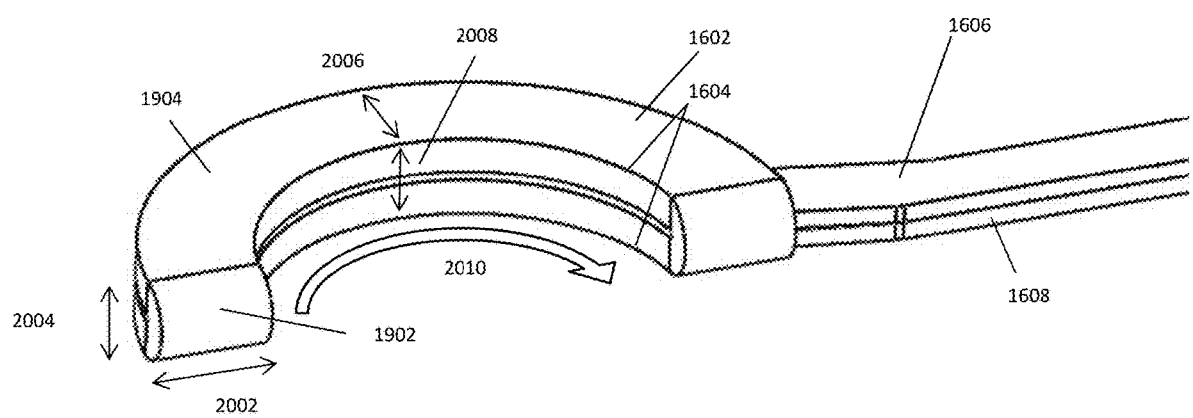
FIG. 20 illustrates an isometric view of the embodiment of FIG. 19, showing a width and height of a device for creating a capsulorhexis.

FIG. 20 shows an isometric view of the device with heights and widths labeled. Where the template enters the incision defines an entry surface 1902 which includes an entry height 2002 and entry width 2004. The entry height 2002 may be in the range of approximately 0.4 mm to 1.25 mm, 0.6 mm to 1.0 mm, or any range or subrange therebetween. The entry width 2004 may between 0.4 mm to 2.0 mm, 1.0 mm to 1.5 mm, or any range or subrange therebetween. The device is then hooked through the corneal incision following an insertion path 2010. The device may have a defined cross-section width 2006 and cross-section height 2008 at any point along the template 1602 as it is inserted through the incision. The cross-section may remain constant as it is inserted or may vary as it is inserted. The cross-section width 2006 and cross-section height 2008 may have dimensions which are similar to the entry width 2004 and entry heights 2002 defined above. For a cross-section width 2006 of 0.75 mm and a cross-section height 2008 of 1.25 mm, the cross-sectional area is about or substantially 0.94 mm$^2$. If a corneal incision is made with a 2.2 mm blade and a round instrument is inserted, the maximum circumference is theoretically 4.4 mm which corresponds to a 1.4 mm diameter instrument and a 1.54 mm$^2$ cross-sectional area. It is therefore possible for the device with a cross-sectional width 2006 of 0.75 mm and a cross-sectional height 2008 of 1.25 mm to be inserted through the incision.

Figure 21:
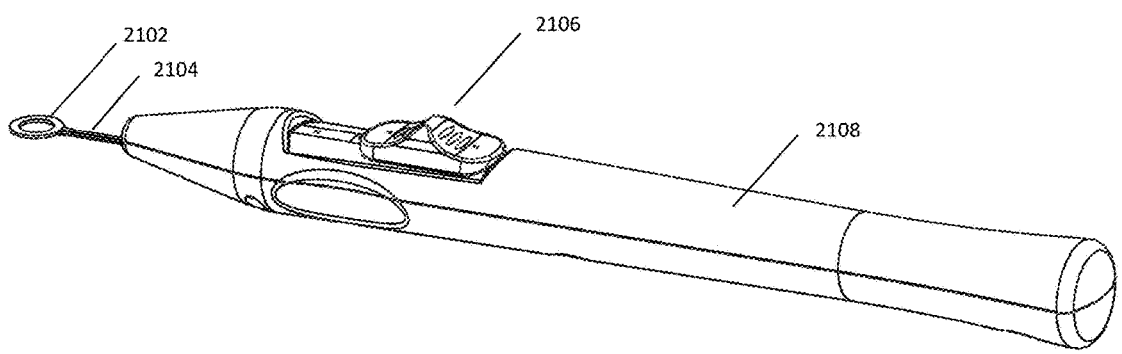
FIG. 21 illustrates an isometric view of an embodiment of a device, with a handle assembly, for creating a capsulorhexis.
Figure 22:
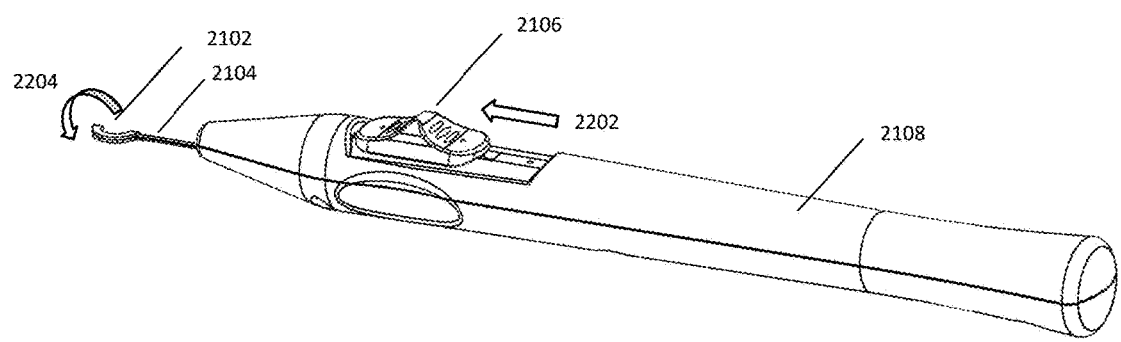
FIG. 22 illustrates the embodiment of FIG. 21 with the device fully bent.

As shown in FIG. 21, an embodiment of the device is shown with a control interface. A handle 2108 is a control interface that provides a mechanism of manipulating the template 2102 within the eye. The connectors 2104 described elsewhere herein are connected to the handle 2108 and a slider 2106 such that as the slider 2106 moves forward and backwards, the template 2102 transitions between a first bent configuration and a second unbent configuration as will be described in greater detail elsewhere herein. As shown in FIG. 21, the slider 2106 is shown in a second position and the template 2102 is shown in the second unbent configuration. In FIG. 22, the slider 2106 has been advanced forward 2202 to a first position and the template 2102 has rotated 2204 to a first bent configuration by the rotation of the connectors 2104.

Figure 23:
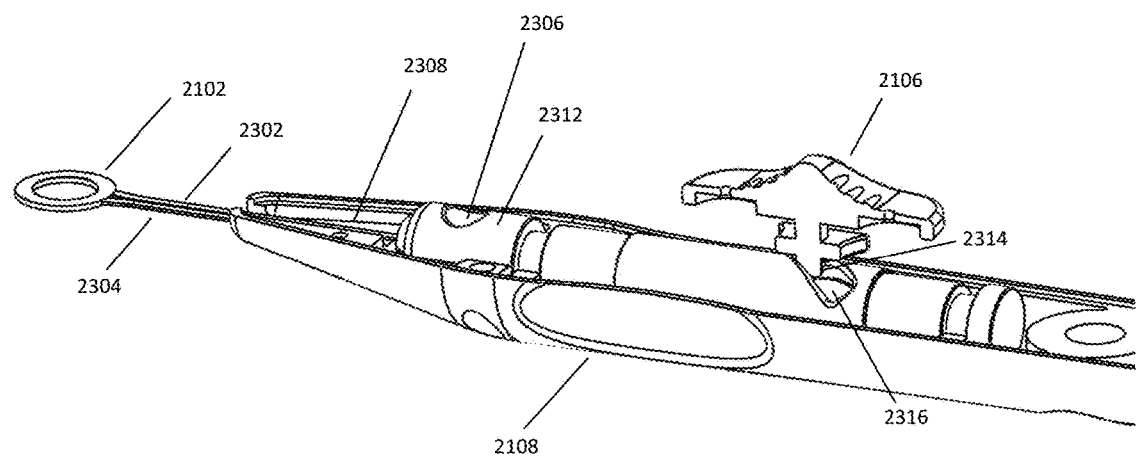
FIG. 23 illustrates a cross-sectional view of the embodiment of FIG. 21.
Figure 24:
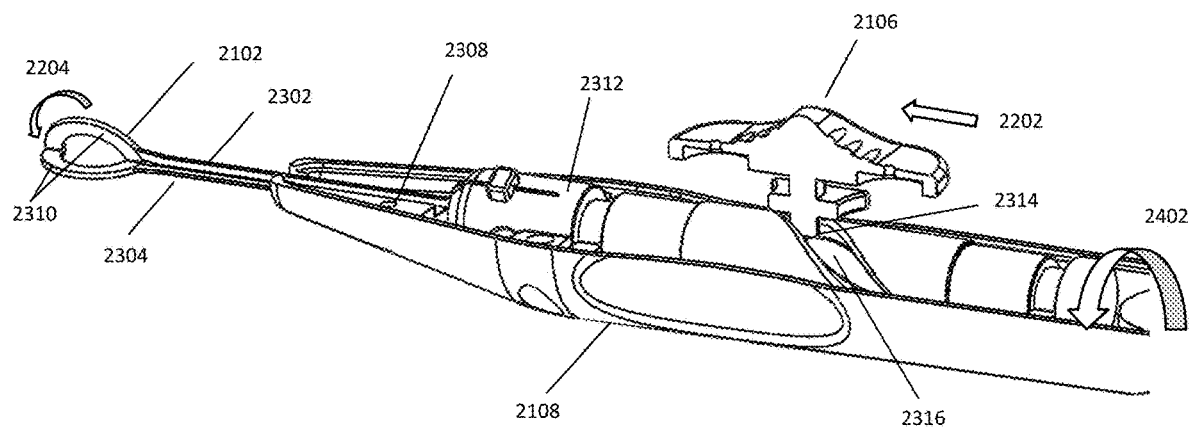
FIG. 24 illustrates a cross-sectional view of the embodiment of FIG. 21 with the slider partially advanced and the device partially bent.
Figure 25:
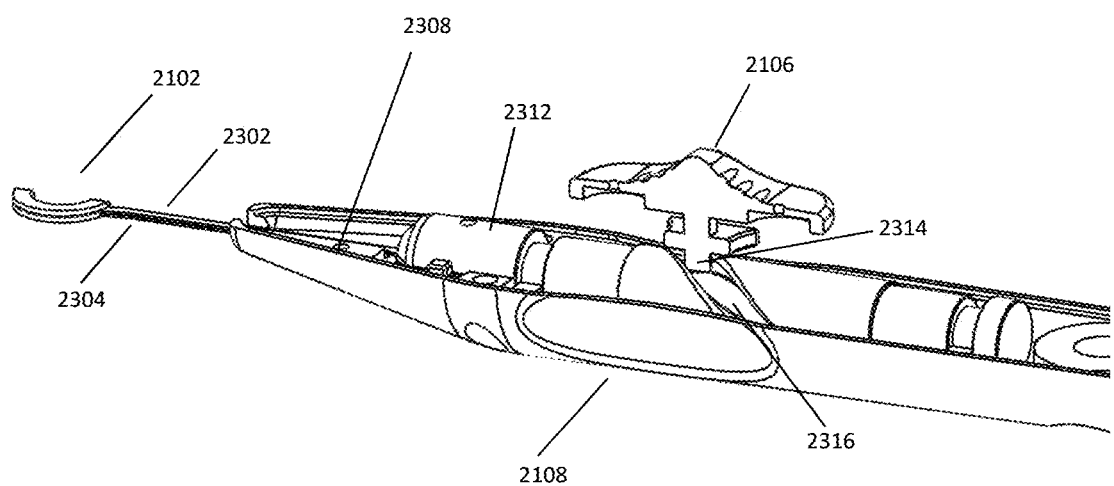
FIG. 25 illustrates a cross-sectional view of the embodiment of FIG. 21 with the slider fully advanced and the device for creating a capsulorhexis mostly bent.

As shown in FIGS. 23-25, an embodiment of a handle 2108 is shown. The handle 2108 is shown in a cross-section about the top plane so that only the bottom half of the handle 2108 is shown. The slider 2106 is shown in a cross-section plane about a right plane so that only the right half of the slider 2106 is shown. The left connector 2304 is attached to a stationary part of the handle 2108 at a left connector attachment 2308 so that it does not rotate. The right connector 2302 is attached to a rotating cam 2312 at a right connector attachment 2306 which is cradled within the handle 2108. The rotating cam 2312 includes a cam path 2316 that engages with a cam post 2314 on the bottom of the slider 2106. As the slider 2106 is advanced forward 2202, the rotating cam 2312 rotates 2402 as defined by the cam post 2314 within the cam path 2316. The cam path 2316 may be arranged to be a simple helical pattern with a constant pitch. In other embodiments, the pitch of the cam path 2316 may vary along its path length. As shown in FIG. 24, the slider 2106 is advanced about half way and the rotating cam 2312 has rotated 70-100 degrees such that the template 2102 is bent into a transitional configuration. In FIG. 25, the slider 2106 is fully advanced and the rotating cam has rotated 160 to 200 degrees so that the template is bent into its first bent configuration. In some embodiments, both connectors 2104 may rotate with neither remaining stationary.

It should be appreciated by one skilled in the art that any number of mechanisms and control interfaces may exist for rotating the connectors 2104. For example, the connectors 2104 may both be attached to rotating pieces that are geared to one another and actuated with an additional gear or rack and pinion type mechanism. Furthermore, motors or other automated mechanisms are contemplated such as pneumatic, electro-magnetic, piezo electric, or any other suitable power transmission mechanism. For example, a motor may be connected to the rotating cam 2312 shown in FIGS. 23-25 such that a button is depressed which controls the movement of the rotating cam 2312 and therefore the configuration of the template 2102. In some embodiments, the control interface is simply the connectors 2104 which extend out of the eye. The user may grasp the connectors 2104 directly and manipulate the location and configuration of the template by manipulation of the connectors 2104.

In some embodiments, the devices described herein are connected to robotic assemblies. Robotic surgery is rapidly expanding in use and certain procedures are well suited for robotic applications. Creating a capsulorhexis with a robotic device by simply mimicking existing manual techniques presents several challenges. The ability to visualize the torn capsulorhexis edge while it is being created is difficult especially for robotic systems. Additionally, the reaction forces while creating the capsulorhexis are very small and therefore may be difficult for a robot to detect. The devices described herein may overcome these challenges by providing a template for the capsulorhexis such that visual feedback and force feedback are not required for creating a repeatable and consistent capsulorhexis. In some embodiments, the devices described herein are attachments for a robotic system. The device is inserted in the eye and the robot actuates the connectors such that the template transitions between a first and second configuration.

In some embodiments, the devices described herein include features which fixate the device to the eye of the patient. For example, a clamping mechanism may be used to secure the device onto the sclera or other ocular structure. Such an embodiment may be beneficial so that the user does not have to hold the device during the capsulorhexis procedure. The device can be used as described herein and positioned on the surface of the capsular bag. The device can then be secured to the eye with a securing feature. The securing feature may include a ring clamp mechanism, a hose clamp mechanism, tissue anchors, screws, or any other suitable mechanism for holding the device on the eye. The user may then let go of the device and use one or both hands for creating the capsulorhexis. In some embodiments, the device is secured on the outside of the eye while in other embodiments the device is secured within the anterior chamber of the eye.

Other materials and geometries for the bendable areas 1706 may be considered. In some embodiments, the bendable area 1706 is defined by a flexible area between the two rigid sections of the template backers. For example, the template backers may be connected at the two bendable areas 1706 by a small elastomeric element that may be folded. In such an embodiment, the tearing profile 1604 may exist for part of the circumference along the inner surface 1612 of the template backers, and then transition to the elastomeric element which defines the bendable areas 1706, and then transitions back to the template backers. Therefore, the tearing profile 1604 does not exist along the edge of a single material or element but rather across several elements. In still other embodiments, the template backers may be connected in the bendable areas 1706 by a hinge mechanism. The hinge mechanism may allow the template backers to fold relative to one another. In such embodiments, the tearing profile 1604 may be defined by the inner surface 1612 of the two or more template backers. Indeed, more than two template backers and hinge mechanisms may exist that allow the device to be configured into a first configuration while inserted into the eye but become a second configuration during the capsulorhexis procedure.

Figure 33:
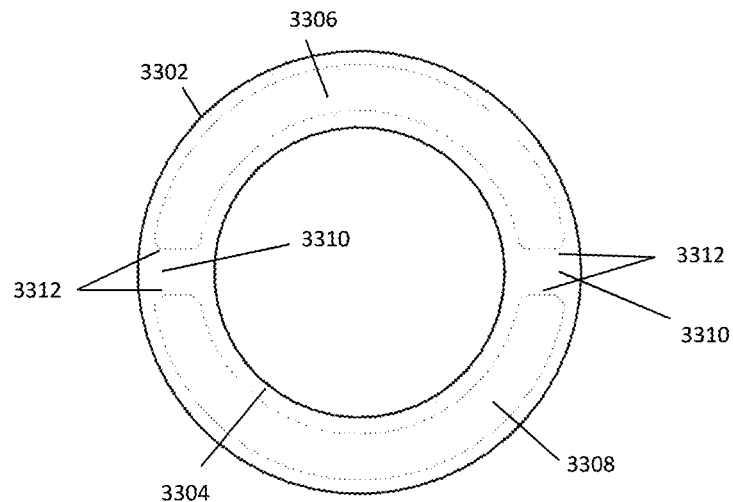
FIG. 33 illustrates a device for creating a capsulorhexis.

The device may include a single connected assembly as described above or may alternatively be a set of tools and pieces. In some embodiments, the template may include one or more bendable areas but may not include connectors. FIG. 33 shows such an embodiment. A template 3302 is shown with a tearing profile 3304, a right template backer 3306, and a left template backer 3308. The space between the template backer ends 3312 creates a bendable area 3310. In such embodiments, the template 3302 may be bent and inserted into the eye through a conical incision. Once inside the eye, a separate instrument that is part of the device and which may connect to the template 3302 may be used. The instrument may include magnets or other features which easily connect to the template 3302 and allow the instrument to manipulate the position of the template 3302 within the eye. The instrument may be inserted through a separate smaller incision while a pair of capsulorhexis forceps are inserted through a larger incision that the template was inserted through. In some embodiments, the template backers may be inserted into the eye, connected to the template 3302 and detached once inside of the anterior chamber.

The templates described herein may be inserted through the conical incision in any number of ways. The template may be part of a hand-held instrument that includes an introducer similar to a cannula that contains the template during the insertion into the eye and then is deployed intraocularly. In such embodiments, the template may be connected to additional control components that allow the hand-held instrument to maneuver the template to the correct position and provide a downward force onto the capsular bag. Alternatively, the template may be inserted with a hand-held instrument but is detached and manipulated with a different instrument, for example a forceps. Alternatively, the template may exist as a completely independent component that is inserted directly into the anterior chamber without the need for a cannula simply by folding it.

The templates described herein may be rolled or folded in any number of ways. Alternatively, the template may disconnect from itself at one or more discrete points along the circumference. In such an embodiment, the template may not need to be folded and may be inserted directly or through a cannula. Upon entry into the anterior chamber the template may be re-connected such that a continuous tearing profile is then re-formed. Alternatively, the template may be inserted into the eye as a connected ring, but when the procedure is complete the template may be broken down into one or more components that allow it to be removed from the eye.

In some embodiments, the templates described herein may only form part of a tearing profile for the capsulorhexis. For example, the template may provide 60 to 120 degrees of a tearing profile of the capsulorhexis. In such an embodiment, the template may be repositioned multiple times as necessary as the surgeon completes the capsulorhexis.

In some embodiments, the templates described herein or associated instruments may include features which are used to center the capsulorhexis. For example, the template may include a set of wires or flexible components that are similar to the haptics on intraocular lenses. The template haptics could be positioned such that they reference off of one or more anatomical features within the anterior chamber. For example, the template haptics may extend radially from the template toward the outer radius of the eye. They may contact the angle of the eye at the root of the iris near the scleral spur. The haptics may provide an evenly distributed force around the template that centers the template relatively to the sclera and cornea such that the template is approximately centered about the optical axis of the eye. Such an embodiment is similar to how the haptics on intraocular lenses work. Other anatomical features may be also used. For example, the inner profile of the iris may be referenced with flexible components extending from the template.

Figure 35A:
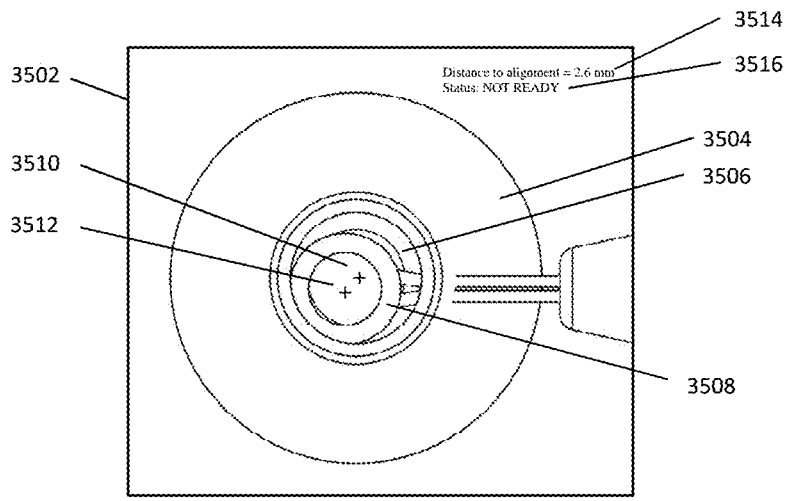
FIG. 35A illustrates a system for creating a capsulorhexis with a control interface showing a substantial offset in axis alignment.
Figure 35B:
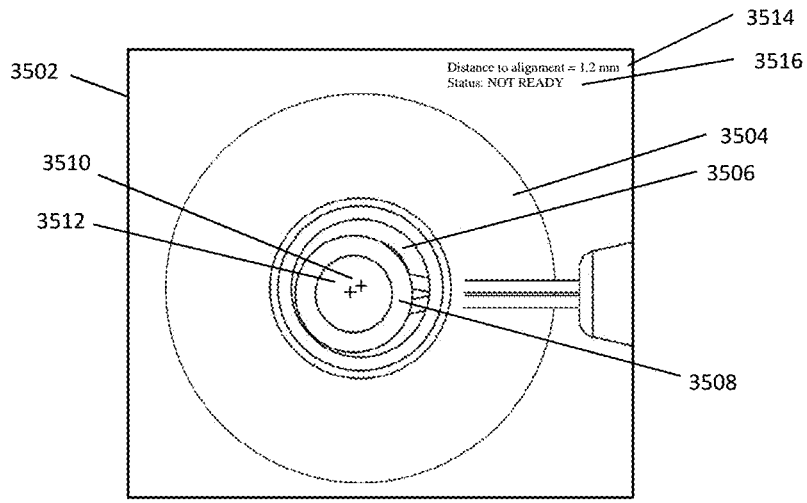
FIG. 35B illustrates a system for creating a capsulorhexis with a control interface showing a moderate offset in axis alignment.
Figure 35C:
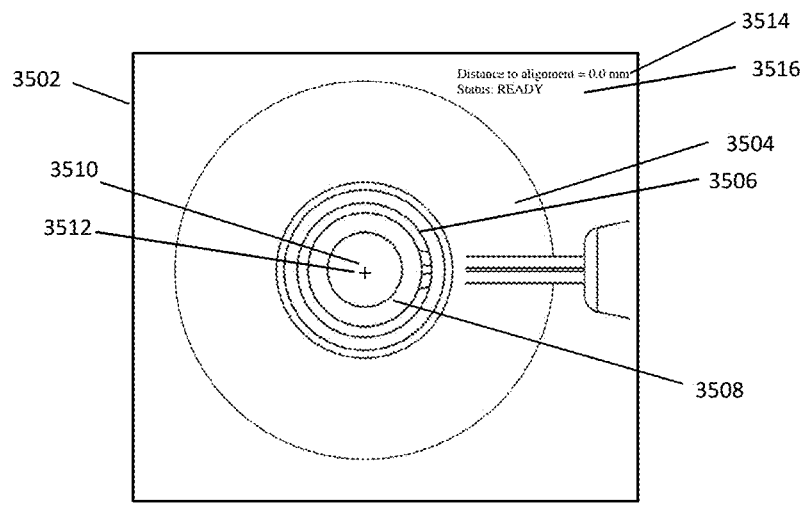
FIG. 35C illustrates a system for creating a capsulorhexis with a control interface showing a minimal offset in axis alignment.

FIGS. 35A-C show an embodiment of a system that includes a feedback mechanism for the surgeon to indicate the relative position of the device to the optic axis 3510 of the eye 3504. Centering the capsulorhexis relative to the optic axis 3510 of the eye 3504 is an important part of the procedure. Therefore, the position of the device is important while the capsulorhexis is being performed. A vision system which includes an ophthalmic microscope is typically used by the surgeon during the procedure. An exemplary user display image 3502 of such a vision system is shown in FIGS. 35A-C. The eye 3504 is shown in a top view including an iris 3506. The template 3508 is within the eye 3504 and has a template central axis 3508 defined by the center of the tearing profile. The vision system may include software that monitors the position of the device within the eye. As shown in FIG. 6, the device may include a right template backer 606 and a left template backer 608 attached to the template 602. The vision system software may identify the template backers and therefore identify their position. The template backers may be a specific color that the vision system recognizes such as purple, or they may include certain fiducials such as cutouts or other reference markers that assist the software in determining their position. For example, the template backers may include various holes that the vision system software may easily identify. Once the vision system has established the location of the template 3508, the software may then determine the distance between the optic axis 3510 of the eye 3504 and template central axis 3512. The user display image 3502 may provide a distance indicator 3514 to the surgeon. The distance indicator 3514 may be a numerical value, a graduated color scale, an audible noise, or any other feedback. The user display image 3502 may further provide a status indicator 3516 that informs the user whether the device is in an adequate position. The embodiment shown in FIGS. 35A-C may include visual feedback in the vision system display that changes color from red when the center of the capsulorhexis profile of the device is relatively far away from the optic axis 3510 and may gradually change to yellow and then green as it is moved closer. Any number of other suitable visual feedback cues may be implemented. Alternatively, audible feedback or haptic feedback may be provided to the user to indicate whether they either need to reposition the device closer to the center of the optic axis 3510 or if they are in a correct position to begin tearing the capsulorhexis.

In some embodiments, suction may be used to position the template described herein onto the capsular bag. For example, the underside of the template may include a vacuum outlet that rests against the capsular bag such that when suction is applied, the template is held against the capsular bag. Additionally or alternatively, irrigation outlets may be included on the template or associated components such that inspiration and/or aspiration may be simultaneously or independently performed.

In some embodiments, the templates described herein may include fluid passageways. The passageways may provide several benefits. In some embodiments, the fluid passageway allows for a fluid to be injected into the eye from a syringe outside the eye. The user may inject viscoelastic, balanced saline solution (BSS), steroids, dyes such as trypan blue, or any other number of fluids which are used in ocular surgery. The fluids may assist in the procedures described herein or may facilitate different procedures. For example, anterior chamber stability is an important factor in cataract surgery. The fluid channels may provide a constant stream of BSS to maintain a given pressure within the anterior chamber. In some embodiments, the fluid channels may be used to hydro-dissect the lens within the capsular bag after the capsulorhexis procedure. In other embodiments, the fluid channels may provide a means of creating a capsulorhexis. In some embodiments, the fluid delivered may be ethanol alcohol which is used as an ablating agent in other surgeries in the body. Ethanol can ablate tissue when injected. In such embodiments, the ethanol alcohol may be injected through the fluid passageways of the device such that it is delivered to the anterior surface of the capsular bag along an ablating profile. The template may remain in intimate contact with the capsular bag during the procedure so a minimal amount of ethanol is required and no additional damage to other ocular structures is observed. The ethanol may ablate the capsular bag along the ablating profile and create a capsulorhexis. In still other embodiments, a high speed fluid is injected through the fluid passageways that may hydro-cut the capsulorhexis. The fluid may be injected at speeds such as seen in needle free injectors, and the fluid may cut the capsulorhexis. The capsulorhexis may be created all at once or in increments. In some embodiments, the fluid passageways may have discrete nozzles that direct the fluid at the capsular bag. The nozzles may be positioned such that a series of holes in the capsular bag is created like perforations on a piece of paper. After creating such holes, the user may simply tear away the center capsular bag material. In other embodiments, the nozzle in the template may be a single continuous ring that creates the capsulorhexis all at once.

In some embodiments, the fluid passageways may provide additional benefits. The fluid dispersed through the passageways may provide rigidity to the template. In some embodiments, the fluid has a low viscosity such as water or saline. The fluid passageway may be closable so that a pressure can be applied to the fluid. As the fluid pressurizes, it may provide rigidity to the structure of the template. Such an embodiment may be advantageous because the template can be inserted into the eye in a first flexible configuration wherein the fluid is not pressurized and then once the template is within the eye, the device transitions to a second stiff configuration that provides the benefits of rigidity described herein. Pressurizing the fluid can transition the template between the first flexible configuration and second rigid configuration. It should be appreciated by one skilled in the art that a fluid may imply a liquid such as water, saline, or viscoelastic but may also imply a gas such as air, argon, nitrogen, or any other suitable gas. In some embodiments, the fluid dispersed in the passageways is a hardening material that can be hardened. Examples of such materials may include two part epoxies, ultraviolet light curable epoxies, or any other material that can transition between a soft and hard state.

In some embodiments, the templates described herein may actually be a template for ablating the capsular bag with light or other energy modalities. In these embodiments, the template may be placed into the anterior chamber and may cover a larger portion of the eye including parts of the iris. The template may leave an opening in the center where a laser capsulotomy will be created with a laser. The laser may be outside the eye and shine onto the exposed capsular bag not covered by the template and create a cut at the profile of the template.

Methods

As shown in FIG. 26-31, a method for creating a capsulorhexis using a template 2602 of one embodiment includes bending the template 2602 into a first bent configuration (FIG. 26), inserting the template 2602 into the eye through a corneal incision 2620 (FIGS. 27-29), unbending the template 2602 into a second unbent configuration (FIG. 30), placing the template 2602 against the anterior surface of the capsular bag 2622 with a pair of template backers (FIG. 31), and then tearing the capsular bag material so that the tear follows the tear profile. The method functions to insert a capsulorhexis template 2602 into the anterior chamber of an eye through a corneal incision 2620 less than 3.0 mm. In some embodiments, the method functions to place a downward force 3110 on a capsulorhexis template 2602 with a right connector 2604 and left connector 2606 that extend through a corneal incision 2620. The method is used for ocular surgery, but may additionally or alternatively be used for any suitable applications, clinical or otherwise. The method may be configured and/or adapted to function for any suitable insertion of a wide instrument through a narrow incision.

Figure 26:
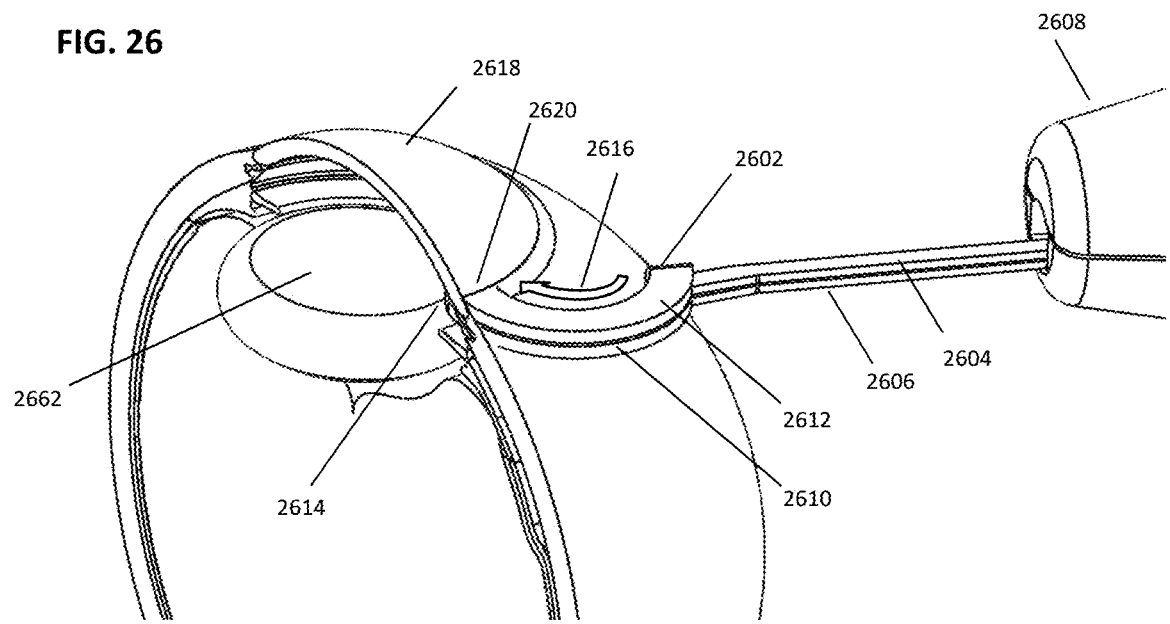
FIG. 26 illustrates an embodiment of a device for creating a capsulorhexis entering an anterior chamber of an eye with the device mostly bent.

As shown in FIG. 26, the template 2602 includes an outer surface 2610, a bottom surface 2612, top surface 3006, and an entry surface 2614. An eye is shown with a cornea 2618, corneal incision 2620, and capsular bag 2622. The template 2602 is bent into a first bent configuration where the right connector 2604 and left connector 2606 are rotated onto each other such that the template 2602 becomes bent about one or more bendable areas 2902. A clear corneal incision 2620 is made in the eye and the eye may be prepared with the infusion of viscoelastic substances to inflate the anterior chamber. The corneal incision 2620 may be less than 3.0 mm, less than 2.2 mm, or any appropriate size that is typical for primary corneal incision 2620 sizes in cataract surgeries. In some embodiments, the corneal incision 2620 may be a smaller incision such as a side port incision which may be 1.5 mm or less. The entry surface 2614 of the bent template 2602 is inserted through the corneal incision 2620 into the eye. The device may be positioned and rotated as shown in FIG. 26 such that cross-sectional area of the template 2602 passing through the corneal incision 2620 is minimized.

Figure 27:
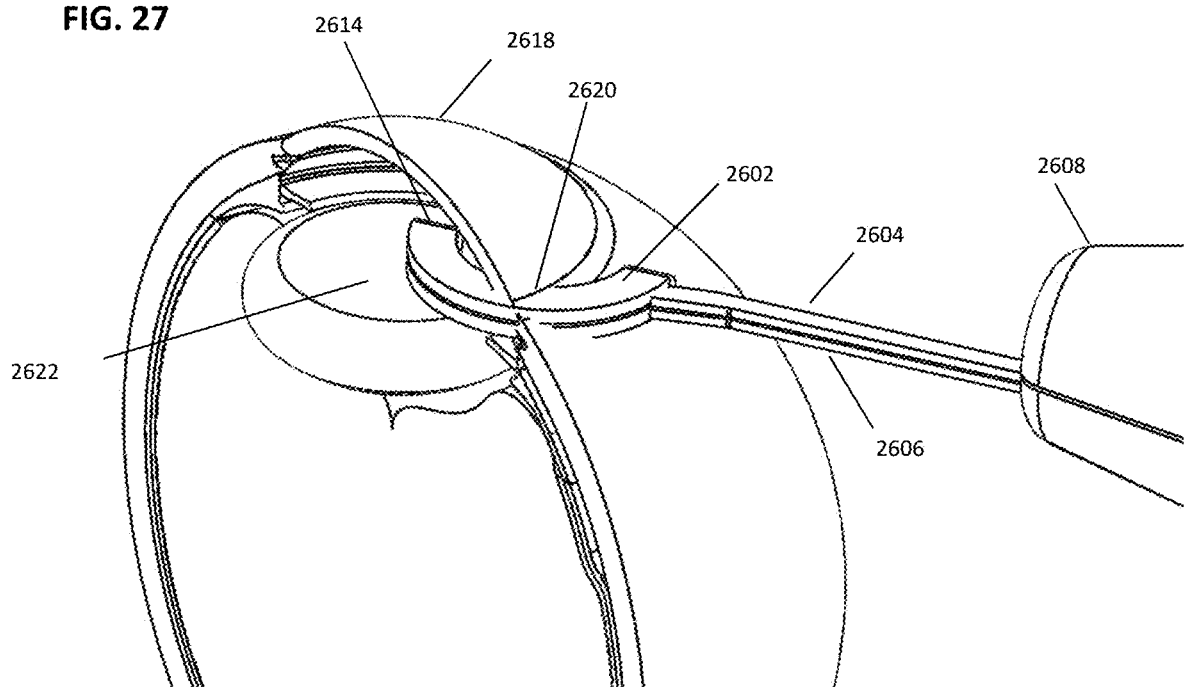
FIG. 27 illustrates the embodiment of FIG. 26 with the device partially advanced into an anterior chamber of an eye.
Figure 28:
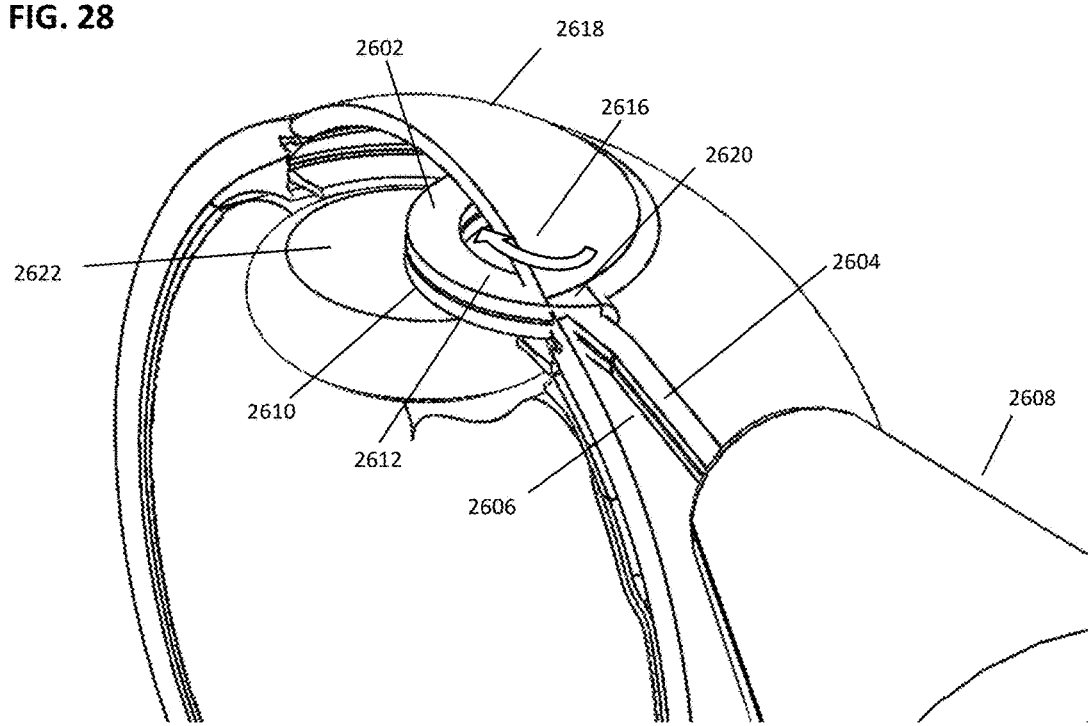
FIG. 28 illustrates the embodiment of FIG. 26 with the device further advanced into an anterior chamber of an eye.

As shown in FIG. 27, the template 2602 is further advanced through the corneal incision 2620 and the device is rotated to keep a minimal cross-sectional area passing through the corneal incision 2620. As shown in FIG. 28, the template 2602 continues to be inserted through the corneal incision 2620 and the device continues to be rotated to minimize the cross-sectional area at the incision site. The device follows an insertion profile 2616 as it is rotated and advanced through the corneal incision 2620.

Figure 29:
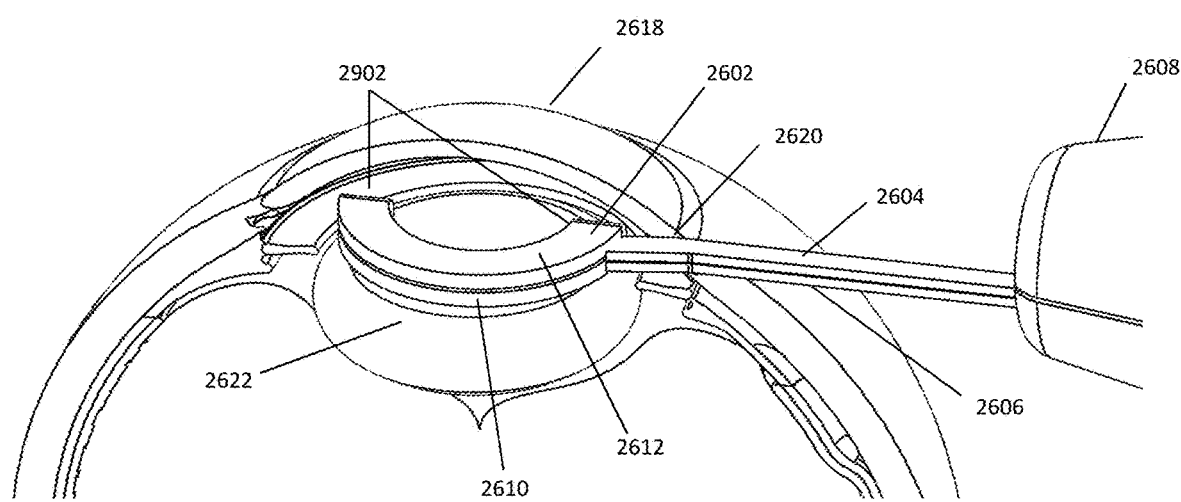
FIG. 29 illustrates the embodiment of FIG. 26 with the device fully within the anterior chamber of an eye.
Figure 31:
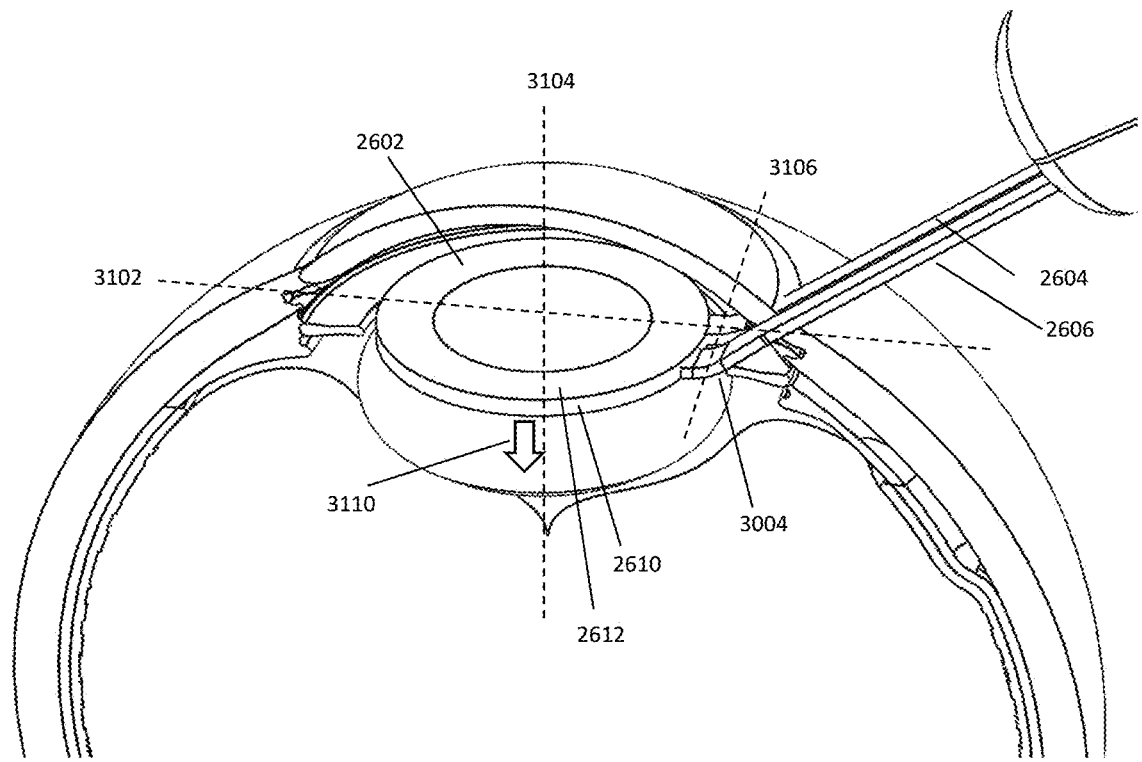
FIG. 31 illustrates the embodiment of FIG. 26 with the device placed against the capsular bag of an eye.

As shown in FIG. 29, the template 2602 is fully within the anterior chamber of the eye and may be unbent into a second unbent configuration. The right connector 2604 and left connector 2606 extending through the corneal incision 2620 may be rotated such that the template 2602 is unbent about the bending axis 3102 (as shown in FIG. 31) within the eye taking care to avoid contacting the corneal endothelial surface. The connectors may be actuated and manipulated manually or a handle 2608 may be utilized to move the connectors to the second configuration.

Figure 30:
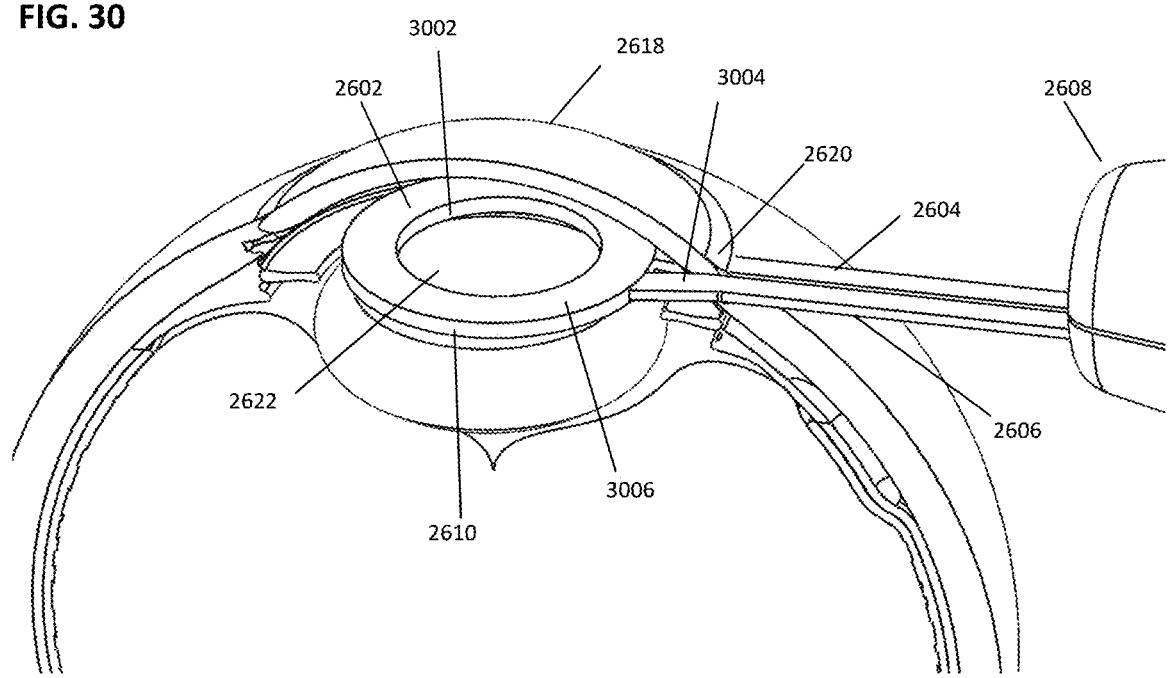
FIG. 30 illustrates the embodiment of FIG. 26 with the device mostly unbent in the anterior chamber of an eye.

As shown in FIG. 30, the template 2602 is unbent into a second unbent configuration above the capsular bag 2622. The user may then place the template 2602 and tearing profile 3002 against the surface of the capsular bag 2622 by moving the device downward or by angling the device such that the template 2602 pivots downward against the capsular bag 2622. As shown in FIG. 31, the template 2602 is shown in intimate contact with the capsular bag 2622 and the connectors are in a flexed state at the flexible area 3004 shown about the flexing axis 3106. The device is centered about the optic axis 3104. The tearing profile 3002 is pressed against the capsular bag 2622 with a downward force 3110 and defining a boundary where the capsular bag 2622 will tear against rather than continue past the tearing profile 3002. The user may then insert a pair of capsulorhexis forceps or other suitable tool through the same incision or a separate incision and grab the capsular bag. As the capsular bag 2622 is torn, the tear first propagates up to the tearing profile 3002 and then as further tension is applied, the tear continues along the perimeter of the tearing profile 3002. The user continues to tear the capsular bag until the tear has continued around the entire perimeter and returns to the starting position. At this point a full capsulorhexis has been created, and the device may be removed from the eye. The template 2602 may be bent back into a first bent configuration similar to what is shown in FIG. 29. The template may then be snaked out of the corneal incision 2620 until the device is removed from the eye.

Figure 36:
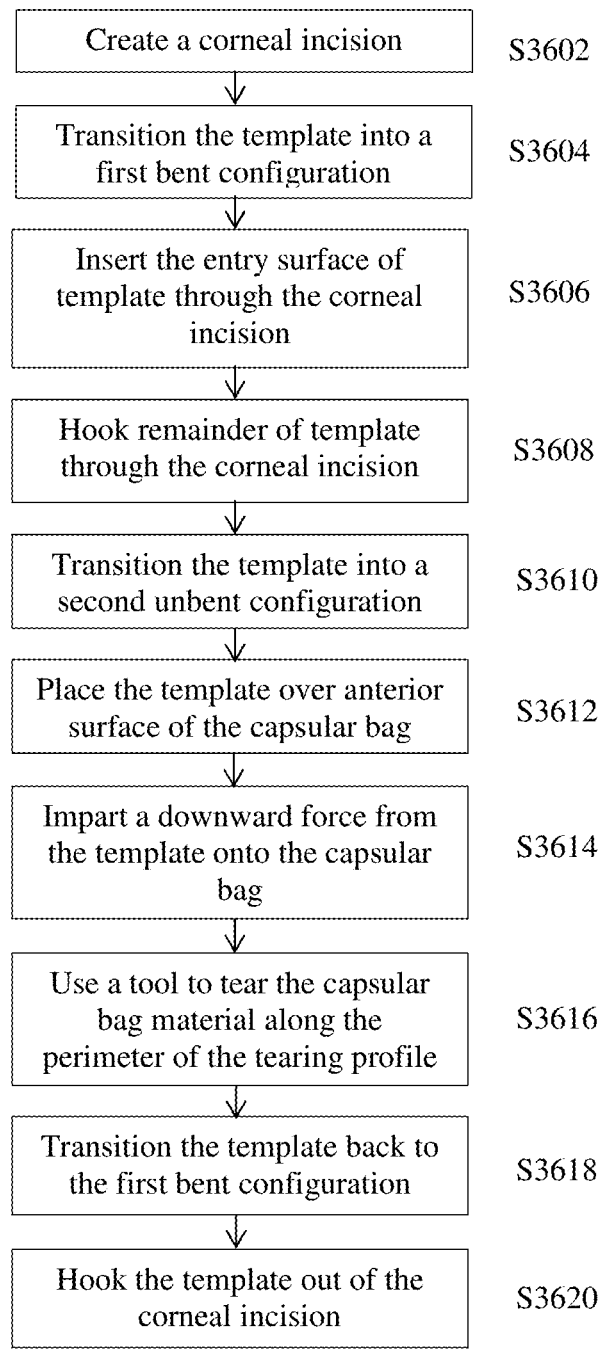
FIG. 36 illustrates a flow chart of a method for creating a capsulorhexis.

FIG. 36 illustrates a flow chart of a method of creating a capsulorhexis. A corneal incision is first created in S3602. A template is then transitioned to a first bent configuration in S3604. The entry surface template is inserted through the corneal incision in S3606. The remainder of the template is then hooked through the corneal incision in S3608. The template is then transitioned into a second unbent configuration in S3610. The template is then placed over the anterior surface of the capsular bag in S3612. The user imparts a downward force onto the template and the capsular bag in S3614. The user then uses a tool to create a capsulorhexis along the perimeter of the tearing profile in S3616. The template is then transitioned back to a first bent configuration in S3618. The template is then hooked out of the eye through the corneal incision in S3620.

In some embodiments, the devices described herein do not include connectors that extend through the incision. In these embodiments, the template may be inserted into the eye by bending it into a first bent configuration as described elsewhere herein but then a separate instrument may be used to manipulate and position the template within the eye onto the capsular bag. For example, an instrument which includes magnetic tips may be inserted to easily snap onto the template backers within the eye.

In some embodiments, the templates described herein may be left in the eye for subsequent steps of the cataract procedure. For example, the template may remain on the top of the capsular bag during hydrodissection of the lens or during the removal of the lens tissue from the eye with or without phacoemulsification. The template may provide further protection from a tear propagating posteriorly or may provide more structure to the bag during the subsequent steps of the procedure.

As used in the description and claims, the singular form "a", "an" and "the" include both singular and plural references unless the context clearly dictates otherwise. For example, the term "template" may include, and is contemplated to include stencil, profile, or pattern. At times, the claims and disclosure may include terms such as "a plurality," "one or more," or "at least one;" however, the absence of such terms is not intended to mean, and should not be interpreted to mean, that a plurality is not conceived.

The term "about" or "approximately" or "generally," when used before a numerical designation or range (e.g., to define a length or pressure), indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a device, substance, or composition.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a system or method consisting essentially of the elements as defined herein would not exclude other materials, features, or steps that do not materially affect the basic and novel characteristic(s) of the claimed disclosure. "Consisting of" shall mean that the devices, systems, and methods include the recited elements and exclude anything more than a trivial or inconsequential element or step. Embodiments defined by each of these transitional terms are within the scope of this disclosure.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A device configured to be positioned against a capsular bag of a patient for creating a capsulorhexis, the device comprising:

a first side comprising a tearing profile;

a second side opposite the first side; and one or more bendable sections defining a first portion and a second portion, wherein the device is transitionable between a first configuration and a second configuration, wherein, in the first configuration, the device is configured to fold about the one or more bendable sections, such that the tearing profile does not define a flat plane, and wherein, in the second configuration, the device is configured to unfold about the one or more bendable sections, such that the tearing profile defines a flat plane.

2. The device of claim 1, wherein, in the first configuration, at least a part of the second side of the first portion is folded adjacent to at least a part of the second side of the second portion.

3. The device of claim 2, further comprising one or more rigid sections in one or more of: the first portion and the second portion, wherein the one or more rigid sections are configured to not bend substantially.

4. The device of claim 3, wherein the one or more rigid sections are each defined by one or more template backers which stiffen the first and second portions.

5. The device of claim 4, wherein the one or more bendable sections are defined by an absence of the one or more template backers.

6. The device of claim 4, wherein the template backers comprise a layer of rigid material on the second side of the template.

7. The device of claim 4, wherein the one or more template backers each include connector elements.

8. The device of claim 7, wherein the connector elements each include a flexing area that is configured to bend to impart a downward force on the capsular bag.

9. The device of claim 6, wherein the rigid material comprises one or more of: stainless steel, Nitinol, plastic, or a combination thereof.

10. The device of claim 4, wherein the one or more template backers are configured to press the first side onto the capsular bag with sufficient force to create a tear in the capsular bag.

11. The device of claim 3, wherein the device comprises two bendable sections and two rigid sections.

12. The device of claim 11, wherein the two bendable sections are configured to bend about a single bending axis.

13. The device of claim 1, wherein, in the second configuration, the tearing profile forms a perimeter for the capsulorhexis.

14. The device of claim 1, wherein, in the first configuration, a maximum cross-sectional area of the device is less than 3.0 mm$^2$.

15. The device of claim 1, wherein the one or more bendable sections comprise one or more of: silicone, thermoplastic elastomer, nitinol, polyurethane, a combination thereof, a local thinning of the one or more, or a local thinning of the combination thereof.

* * * * *